(12) United States Patent
Schottek et al.

(10) Patent No.: US 6,861,384 B2
(45) Date of Patent: Mar. 1, 2005

(54) PROCESS FOR PREPARATION OF A SALT-LIKE CHEMICAL COMPOUND AND ITS USE IN CATALYST SYSTEMS FOR PREPARING POLYOLEFINS

(75) Inventors: Jörg Schottek, Frankfurt (DE); Gerhard Erker, Münster (DE); Gerald Kehr, Münster (DE)

(73) Assignee: Basell Polyolefine GmbH, Wesseling (DE)

( * ) Notice: Subject to any disclaimer, the term of this patent is extended or adjusted under 35 U.S.C. 154(b) by 39 days.

(21) Appl. No.: 10/659,163

(22) Filed: Sep. 10, 2003

(65) Prior Publication Data

US 2004/0048992 A1 Mar. 11, 2004

Related U.S. Application Data

(62) Division of application No. 09/798,859, filed on Feb. 22, 2001, now abandoned.

(30) Foreign Application Priority Data

Mar. 17, 2000 (DE) .......................................... 100 13 043

(51) Int. Cl.$^7$ .............................. C08F 4/64; C07F 5/02; C07F 5/05
(52) U.S. Cl. ........................... 502/123; 568/1; 556/176; 502/103; 502/152; 526/134; 526/160; 526/135; 526/943; 526/133
(58) Field of Search .............................. 568/1; 502/123, 502/103, 152; 526/134, 160, 133, 943

(56) References Cited

U.S. PATENT DOCUMENTS 5,384,299 A 1/1995 Turner et al. ................ 502/155

FOREIGN PATENT DOCUMENTS

| DE | 3543360 | 11/1987 | ........... C08F/10/02 |
|----|---------|---------|---------|
| EP | 0107127 | 5/1984 | ........... C08F/10/00 |
| EP | 0129368 | 12/1984 | ........... C08F/10/00 |
| EP | 0416815 | 3/1991 | ........... C08F/10/00 |
| EP | 0427697 | 5/1991 | ........... C08F/4/602 |
| EP | 0520732 | 12/1992 | ........... C08F/10/00 |
| EP | 0545304 | 6/1993 | ........... C07F/17/00 |
| EP | 0558158 | 9/1993 | ........... C07F/17/00 |
| EP | 0561479 | 9/1993 | ........... C07F/17/00 |
| EP | 0576970 | 1/1994 | ........... C07F/17/00 |
| EP | 0632063 | 1/1995 | ......... C08F/210/02 |
| EP | 0636636 | 2/1995 | ........... C08F/10/02 |
| EP | 0659758 | 6/1995 | ........... C07F/17/00 |
| EP | 0661300 | 7/1995 | ........... C08F/10/00 |
| WO | 9524268 | 9/1995 | ............ B01J/31/02 |
| WO | 9822486 | 5/1998 | ........... C07F/17/00 |
| WO | 9964476 | 12/1999 | ........... C08F/4/603 |

OTHER PUBLICATIONS

H. H. Brintzinger et al., "Stereospezifische Olefinpolymerisation mit chiralen Metallocenkatalysatoren;" *Angew. Chem.*, 107: 1255–1283 (1995) (DE) (English Abstract).

H. Sinn et al., "Scope of Ziegler Catalysis;"*Advances in Organometallic Chemistry*, 18: 99–149 (1980).

X. Yang et al., "'Cation–like' Homogeneous Olefin Polymerization Catalysts Based upon Zirconocene Alkyls and Tris(pentafluorophenyl)borane;" *J. Am. Chem. Soc.*, 113: 3623–3625 (1991).

D. H. McConville et al., "Polymerization of α–Olefins by Chelating Diamide Complexes of Titanium;" *Macromolecules*, 29: 5241–5243 (1996).

D. H. McConville et al., Living Polymerization of α–Olefins by Chelating Diamide Complexes of Titanium; *J. Am. Chem. Soc.*, 118: 10008–10009 (1996).

M. Brookhart et al., "New Pd(II)– and Ni(II)–Based Catalysts for Polymerization of Ethylene and α–Olefins;" *J. Am. Chem. Soc.*, 117: 6414–6415 (1995).

M. Brookhart et al., "Copolymerization of Ethylene and Propylene with Functionalized Vinyl Monomers by Palladium(II) Catalyts;" *J. Am. Chem. Soc.*, 118: 267–268 (1996).

M. Brookhart et al., "Highly Active Iron and Cobalt Catalysts for the Polymerization of Ethylene;" *J. Am. Chem. Soc.*, 120: 4049–4050 (1998).

V. C. Gibson et al., "Novel olefin polymerization catalysts based on iron and cobalt;" *Chem. Commun.*, 849–850 (1998).

Bodo Temme et al., "Oxidative $\eta^2$–iminoacyl formation by reaction of amidozirconocene complexes with tris(pentafluorophenyl)borane;" *J. of Organomet. Chem.*, 448: 177–182 (1995).

D. Röttger et al., "Reaction of dimethylzirconocene with imidazole in the prescence of tris(penta–fluorophenyl)borane," *Journal of Organometallic Chemistry*, 518(1), pp. 17–19 (1996).

N. Metzler et al., "Synthesis of a silylene–borane adduct and its slow conversion to a silylborane;" *Chem. Commun.*, 23, pp. 2657–2658 (1996).

J. Galsworthy et al., "Reactions of transition–metal oxo complexes with B(C$_6$F$_5$)$_3$: crystal structures of . . . ," *J. Chem. Soc.*, 8, pp. 1309–1313 (1997).

G. Kehr et al., "Protonation of the Heterocyclic Cp–Anion Equivalent [Pyrrolyl–B(C$_6$F$_5$)$_3$]Li–Formation of a Useful Neutral . . . " *Eur. J. Inorg. Chem.*, 2, pp. 535–538 (2001).

Primary Examiner—Caixia Lu

(57) ABSTRACT

A process for preparing salt-like compounds of the formula (1),

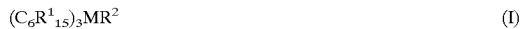

where
R$^1$ are identical or different and are each a hydrogen atom, a halogen atom, C$_1$–C$_{20}$-alkyl, C$_6$–C$_{14}$-aryl, C$_1$–C$_{10}$-alkoxy, C$_2$–C$_{10}$-alkenyl, C$_7$–C$_{20}$-arylalkyl, C$_7$–C$_{20}$-alkylaryl, C$_6$–C$_{10}$-aryloxy, C$_1$–C$_{10}$-haloalkyl, C$_6$–C$_{10}$-haloaryl, C$_2$–C$_{10}$-alkynyl or C$_3$–C$_{20}$-alkylsilyl,
M is an element of main group III of the Periodic Table of the Elements, and
R$^2$ is a substituted or unsubstituted heterocycle,
and the use of such compounds in catalyst systems for preparing polyolefins.

7 Claims, No Drawings

PROCESS FOR PREPARATION OF A SALT-LIKE CHEMICAL COMPOUND AND ITS USE IN CATALYST SYSTEMS FOR PREPARING POLYOLEFINS

CROSS-REFERENCE TO RELATED APPLICATIONS

This application is a divisional of application Ser. No. 09/798,859 filed on Feb. 22, 2001, now abandoned, which claims the benefit of German Patent Application 10013043.7 filed Mar. 17, 2000. The entire contents of application Ser. No. 09/798,859 and German Patent Application No. 10013043.7, each as filed, are incorporated herein by reference.

DESCRIPTION

The present invention relates to salt-like chemical compounds which in combination with an organometallic compound of a transition metal can form a catalyst system which can advantageously be used for the polymerization of olefins, to a process for preparing them and to their use in catalyst systems for preparing polyolefins.

Catalysts of the Ziegler type based on angled metallocenes containing metals of group 4 of the Periodic Table of the Elements form a new generation of industrially usable catalysts for the polymerization of α-olefins (H. H. Brintzinger, D. Fischer, R. Mülhaupt, R. Rieger, R. Waymouth, Angew. Chen. 1995, 107, 1255–1283)

To obtain an active catalyst system, the metallocene complex is treated with a large excess of methylaluminoxane (MAO) (H. Sinn, W. Kaminsky, Adv. Organomet. Chem., 1980, 18, 99). Apart from the high cocatalyst costs, this has the disadvantage of a high aluminum content in the polymer obtained. New activation methods which make do without a superstoichiometric amount of activator nave therefore been developed.

The synthesis of "cation-like" metallocene polymerization catalysts is described in J. Am. Chem. Soc. 1991, 113, 3623 In this, alkyl abstraction from an alkyl-metallocene compound Lakes place by means of trispentafluorophenylborane, which is used in a stoichiometric amount based on the metallocene.

EP-A-0 427 697 describes this synthetic principle and a corresponding catalyst system comprising an uncharged metallocene species (e.g. $Cp_2ZrMe_2$), a Lewis acid (e.g. $B(C_6F_5)_3$) and aluminum alkyls. A process for preparing salts of the formula $LMX^+ XA^-$ according to the above-described principle is described in EP-A-0 520 732.

EP-A-0 558 158 describes zwitterionic catalyst systems which are prepared from dialkyl-metallocene compounds and salts of the formula $[R_3NH]^+[BPh_4]^-$. The reaction of such a salt with, for example, $Cp_2^*ZrMe_2$ results in protolysis with elimination of methane to give a methyl-zirconocene cation as an intermediate. This reacts via C—H activation to give the zwitterion $Cp_2^*Zr^+\text{-}(m\text{-}C_6H_4)$—$BPh_3^-$. Here, the Zr atom is covalently bound to a carbon of the phenyl ring and is stabilized via an agostic hydrogen bond.

U.S. Pat. No. 5,384,299 describes corresponding systems, using dimethylanilinium salts with perfluorinated tetraphenylborates.

In addition to their activating effect, the borate salts have, due to their ligand sphere, a great influence on the reaction equilibrium. Large bulky ligands effectively prevent dimerization of the metallocenium fragments and thus shift the equilibrium to the side of the catalytically active species. The mononuclear borate anions described hitherto have four aryl ligands and can exercise an influence on the reaction equilibrium when bulky groups are incorporated on the ligand (WO 95/24268). Disadvantages of these systems are the complicated syntheses and the extreme sensitivity of the resulting metallocenium complexes.

In addition, most of the starting materials are suspected of being carcinogenic, mutagenic or extremely toxic. Furthermore, the formation of the cationic metallocene species is accompanied by the liberation of amines which is undesirable because of the toxicity of many amines. The sometimes extreme insolubility of the ammonium tetraphenylborates described hitherto also leads to incompletely reacted catalyst systems. This has direct effects on the productivities of the catalyst systems in respect of the amount of metallocene and cocatalyst used. High costs and thus only restricted commercial utilization are the consequence.

WO 99/64476 describes ionic catalyst systems which are activated with a Lewis acid-base complex.

It is an object of the present invention to provide a salt like chemical compound which has the advantages of bulky ligands but avoids the disadvantages of the known compounds of the ammonium salt type.

We have found that this object is achieved by the salt-like chemical compounds of the formula (I). The present invention accordingly provides compounds of the formula $$(C_6R^1{}_5)_3MR^2 \quad (I)$$

where

R$^1$ are identical or different and are each a hydrogen atom, a halogen atom, $C_1$–$C_{20}$C-alkyl, $C_6$–$C_{14}$-aryl, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{10}$-haloalkyl, $C_6$–$C_{10}$-haloaryl, $C_2$–$C_{10}$-alkynyl or $C_3$–$C_{20}$-alkylsilyl, M is an element of main group III of the Periodic Table of the Elements, and R$^2$ is a substituted or unsubstituted heterocycles The present invention also provides a process for preparing the novel compounds of the formula (I), in which compounds of heterocycles R$^2$ containing elements of rain group I or II of the Periodic Table of the Elements are firstly reacted with compounds of the formula $(C_6R^1{}_5)_3M$ in a solvent to form compounds of the formula $[(C_6R^1{}_5)_3MR^2]^+$ which are subsequently protonated by reaction with a proton donor, where R$^1$, M and R$^2$ are as defined in formula (I).

In addition, the invention provides catalyst systems comprising at least one organometallic compound (A) of a transition metal, at least one compound of the formula (I), if desired an alkyl compound (B) of an element of group III or IV of the Periodic Table of the Elements and, if desired, at least one support component (C).

The present invention additionally provides a process for the polymerization of olefins, in which a catalyst system according to the present invention comprising at least one organometallic compound (A) of a transition metal, at least one chemical compound of the formula (I), if desired an alkyl compound (R) of an element of main group III or IV of the Periodic Table of the Elements and, if desired, at least one support component (C) is used. For the purposes of the present invention, polymerization encompasses both homopolymerization and copolymerization.

According to the present invention, preference is given to compounds of the formula (I) in which the element M is aluminum or boron, of which boron is in turn particularly preferred.

In a preferred embodiment of the compounds of the formula (I), the radicals $R^1$ are, independently of one another, halogen atoms, in particular fluorine or chlorine, of which fluorine is in turn particularly preferred.

Particularly preferred halogenated compounds of the formula (I) contain
pentafluorophenyl, 2,3,4,6-tetrafluorophenyl,
2,3,5,6-tetrafluorophenyl, 2,3,5-trifluorophenyl,
2,3,6-trifluorophenyl, 1,3-difluorophenyl,
2,3,5,6-tetrafluoro-4-methylphenyl or
2,3,4,6-tetrafluoro-5-tethylphenyl as $C_6R^1_5$ radical.

In the compounds of the formula (I), the heterocycle generally has a positive charge.

Heterocycles $R^2$ which are preferred according to the present invention are heterocycles having 5- or 6-membered rings. The heterocycles $R^2$ preferably contain one or two heteroatoms. A preferred heteroatom is the nitrogen atom.

Heterocycles which are preferred according to the present invention are pyrrolium, indolium or imidazolium. These can be present in substituted or unsubstituted form in the compounds of the formula (I).

In compounds of the formula (I) which are preferred according to the present invention, the heterocycle $R^2$ is unsubstituted or substituted by a least one halogen atom, $C_1$–$C_{20}$-alkyl, $C_6$–$C_{14}$-aryl, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{20}$-haloalkyl, $C_6$–$C_{14}$-haloaryl, $C_2$–$C_{10}$-alkynyl or $C_3$–$C_{20}$-alkylsilyl. $R^2$ is particularly preferably unsubstituted or substituted by $C_1$–$C_{20}$-alkyl, e.g. methyl, ethyl, isopropyl or tert-butyl, $C_6$–$C_{14}$-aryl or halogen atoms, e.g. fluorine or chlorine, preferably fluorine. $R^2$ is very particularly preferably unsubstituted. Chemical compounds of the formula (I) which are particularly preferred according to the present invention are:
pyrrolium tris(pentafluorophenyl)borate,
pyrrolium tris(heptafluoronaphthyl)borate,
2,4-methylpyrrolium tris(pentafluorophenyl)borate,
2,4-fluoropyrrolium tris(pentafluorophenyl)borate,
2,4-methylpyrrolium tris(heptafluoronaphthyl)borate,
2,4-tert-butylpyrrolium tris(pentafluorophenyl)borate,
2,4-tert-butylpyrrolium tris(heptafluoronaphthyl)borate,
2,4-isopropylpyrrolium tris(pentafluorophenyl)borate,
2,4-isopropylpyrrolium tris(heptafluoronaphthyl)borate,
3,4-methylpyrrolium tris(pentafluorophenyl)borate,
3,4-fluoropyrrolium tris(pentafluorophenyl)borate,
3,4-methylpyrrolium tris(heptafluoronaphthyl)borate,
3,4-tert-butylpyrrolium, tris(pentafluorophenyl)borate,
3,4-tert-butylpyrrolium tris(heptafluoronaphthyl)borate,
3,4-isopropylpyrrolium tris(pentafluorophenyl)borate,
3,4-isopropylpyrrolium tris(heptafluoronaphthyl)borate,
2-methylpyrrolium tris(pentafluorophenyl)borate,
3-methylpyrrolium tris(heptafluoronaphthyl)borate,
2-tert-butylpyrrolium tris(pentafluorophenyl)borate,
3-tert-butylpyrrolium, tris(heptafluoronaphthyl)borate,
2-isopropylpyrrolium tris(pentafluorophenyl)borate,
3-isopropylpyrrolium tris(heptafluoronaphthyl)borate,
pyrrolium tris(2,3,5,6,7,8-hexafluoronaphthyl)borate,
pyrrolium tris(2,4,5,6,7,8-hexafluoronaphthyl)borate,
pyrrolium tris(3,4,5,6,7,8-hexafluoronaphthyl)borate,
pyrrolium tris(2,3,4,6,7,8-hexafluoronaphthyl)borate,
pyrrolium tris(2,3,4,5,7,8-hexafluoronaphthyl)borate,
pyrrolium tris(2,3,5,6,7,8-hexafluoro-4-methylnaphthyl)borate,
pyrrolium tris(2,4,5,6,7,8-hexafluoro-3-methylnapthyl)borate,
pyrrolium tris(3,4,5,6,7,8-hexafluoro-2-methylnaphthyl)borate,
pyrrolium tris(2,3,4,6,7,8-hexafluoro-5-methylnaphthyl)borate,
pyrrolium tris(2,3,4,5,7,8-hexafluoro-6-methylnaphthyl)borate,
pyrrolium tris(nonafluorobiphenyl)borate,
pyrrolium tris(2,2',3,3',5,5',6,6'-octafluorobiphenyl)borate,
pyrrolium tris(3,3',4,4',5,5',6,6'-octafluorobiphenyl)borate,
pyrrolium tris(2,2',4,4',5,5',6,6'-octafluorobiphenyl)borate,
pyrrolium tris(2,2',3,3',4,4',6,6'-octafluorobiphenyl)borate,
pyrrolium tris(2,2',3,3',4,4',5,5'-octafluorobiphenyl)borate,
pyrrolium tris(2,2',3,3',5,5',6,6'-octafluorobiphenyl)borate,
pyrrolium tris(3,3',4,4',5,5',6,6'-octafluorobiphenyl)borate,
pyrrolium tris(2,2',4,4',5,5',6,6'-octafluorobiphenyl)borate,
pyrrolium tris(2,2',3,3',4,4',6,6'-octafluoro-5,5'-methylbiphenyl)borate,
pyrrolium tris(2,2',3,3',4,4',5,5'-octafluoro-6,6'-methylbiphenyl)borate,
pyrrolium tris(2,2',3,3',5,5',6,6'-octafluoro-4,4'-biphenyl)borate,
pyrrolium tris(3,3',4,4',5,5',6,6'-octafluoro-2,2'-biphenyl)borate,
pyrrolium tris(2,2',4,4',5,5',6,6'-octafluoro-3,3'-biphenyl)borate,
pyrrolium tris(2,3,4,6-tetrafluorophenyl)borate,
pyrrolium tris(2,3,5,6-tetrafluorophenyl)borate,
pyrrolium tris(2,3,5-trifluorophenyl)borate, pyrrolium tris(2,3,6-trifluorophenyl)borate, pyrrolium tris(1,3-difluorophenyl)borate, pyrrolium tris(2,3,5,6-tetrafluoro-4-methylphenyl)borate,
pyrrolium tris(2,3,4,6-tetrafluoro-5-methylphenyl)borate,
pyrrolium tris(4-methoxy-2,3,5,6-tetrafluorophenyl)borate,
pyrrolium tris(3-methoxy-2,4,5,6-tetrafluorophenyl)borate,
pyrrolium tris(2-methoxy-3,4,5,6-tetrafluorophenyl)borate,
pyrrolium tris(2,6-difluoro-3-methylphenyl)borate,
pyrrolium tris(2,4-difluoro-5-methylphenyl)borate,
pyrrolium tris(3,5-difluoro-2-methylphenyl)borate, In the process of the present invention for preparing the compounds (I), the elements of main group I or II of the Periodic Table which are used are preferably lithium, sodium., potassium and/or magnesium. Solvents which are suitable for use in the process of the present invention are, in particular, hydrocarbons and ethers. Particularly preferred solvents are ethers such as diethyl ether and THF and hydrocarbons, in particular toluene. Proton donors which can be used according to the present invention are, in particular, inorganic or organic acids, preferably inorganic acids, in particular HCl and $H_2SO_4$.

In the catalyst systems of the present invention, the organometallic transition metal compounds (A) used are, for example, metallocene compounds. These can be, for example, bridged or unbridged biscyclopentadienyl complexes as are described, for example, in EP-A-0 129 368, EP-A-0 561 479, EP-A-0 545 304 and EP-A-0 576 970. Also suitable are monocyclopentadienyl complexes such as bridged amidocyclopentadienyl complexes as described, for example, in EP-A-0 416 815, and also multinuclear cyclopentadienyl complexes as are described, for example, in EP-A-0 632 063. Further suitable organometallic compounds (A) are π-ligand-substituted tetrahydropentalenes as described, for example, in EP-A-0 659 758 and π-ligand-substituted tetrahydroindenes as described, for example, in EP-A-0 661 300. It is also possible to use organometallic compounds in which the complexing ligand contains no cyclopentadienyl radicals. Examples of such compounds are diamine complexes of elements of transition groups III and IV of the Periodic Table of the Elements, as are described, for example, in D. H. McConville, et al, Macromolecules, 1996, 29, 5241 and D. H. McConville, et al, J. Am. Chem. Soc., 1996, 118, 10008. In addition, it is possible to use diimine complexes of elements of transition group VIII of the Periodic Table of the Elements (e.g. $Ni^{2-}$ or $Pd^{2+}$ complexes), as are described in Brookhart et al, J. Am. Chem. Soc. 1995, 117, 6414 and Brookhart et al, J. Am. Chem. Soc., 1996, 118, 267. Use can also be made of 2,6-bis(imino)pyridyl complexes of elements of transition group VIII of the Periodic Table of the Elements (e.g. $Co^{2+}$ or $Fe^{2+}$ complexes), as are described in Brookhart et al, J. Am. Chem. Soc. 1998, 120, 4049 and Gibson et al, Chem. Commun. 1998, 849. Furthermore, it is possible to use metallocene complexes whose complexing ligand contains heterocycles. Examples of such compounds are described in WO 98/22486.

Preferred metallocene compounds are unbridged or bridged compounds of the formula (II),

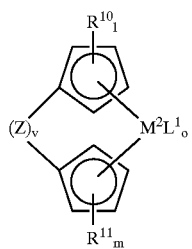

II where $M^2$ is a metal of transition group III, IV, V or VI of the Periodic Table of the Elements, in particular Ti, Zr or Hf, $R^{10}$ are identical or different and are each a hydrogen atom or $Si(R^{12})_3$, where $R^{12}$ are identical or different and are each a hydrogen atom or a $C_1-C_{40}$ group, preferably $C_1-C_{20}$-alkyl, $C_1-C_{10}$-fluoroalkyl, $C_1-C_{10}$-alkoxy, $C_6C_{20}$-aryl, $C_6-C_{10}$-fluoroaryl, $C_5-C_{10}$-aryloxy, $C_2-C_{10}$-alkenyl, $C_7-C_{40}$-arylalkyl, $C_7-C_{40}$-alkylaryl or $C_8-C_{40}$-arylalkenyl, or $R^{10}$ is a $C_1-C_{30}$ group, preferably $C_1-C_{25}$-alkyl such as methyl, ethyl, tert-butyl, cyclohexyl or octyl, $C_2-C_{25}$-alkenyl, $C_3-C_{15}$-alkylalkenyl, $C_6-C_{24}$-aryl, $C_5-C_{24}$-heteroaryl, $C_7-C_{30}$-arylalkyl, $C_7-C_{30}$-alkylaryl, fluorinated $C_1-C_{25}$-alkyl, fluorinated $C_6-C_{24}$-aryl, fluorinated $C_7-C_{30}$-arylalkyl, fluorinated $C_7-C_{30}$-alkylaryl or $C_1-C_{12}$-alkoxy, or two or more radicals $R^{10}$ may be joined to one another in such a way that the radicals $R^{10}$ and the atoms of the cyclopentadienyl ring which correct them form a $C_4-C_{24}$ ring system which may in turn be substituted, $R^{11}$ are identical or different and are each a hydrogen atom or $Si(R^{12})_3$, where $R^{12}$ are identical or different and are each a hydrogen atom or a $C_1-C_{40}$ group, preferably $C_1-C_{20}$-alkyl, $C_1-C_{10}$-fluoroalkyl, $C_1-C_{10}$-alkoxy, $C_6-C_{14}$-aryl, $C_6-C_{10}$-fluoroaryl, $C_6-C_{10}$-aryloxy, $C_2-C_{10}$-alkenyl, $C_7-C_{40}$-arylalkyl, $C_7-C_{40}$-alkylaryl or $C_8-C_{40}$-arylalkenyl, or $R^{11}$ is a $C_1-C_{30}$ group, preferably $C_1-C_{25}$-alkyl such as methyl, ethyl, tert-butyl, cyclohexyl or octyl, $C_2-C_{25}$-alkenyl, $C_3-C_{15}$-alkylalkenyl, $C_6-C_{24}$-aryl, $C_5-C_{24}$-heteroaryl, $C_5-C_{24}$-alkylheteroaryl, $C_5C_{24}$-arylheteroaryl, $C_7-C_{30}$-arylalkyl, $C_7-C_{30}$-alkylaryl, fluorinated $C_1-C_{25}$-alkyl, fluorinated $C_6-C_{24}$-aryl, fluorinated $C_7-C_{30}$-arylalkyl, fluorinated $C_7-C_{30}$-alkylaryl or $C_1-C_{12}$-alkoxy, or two or more radicals $R^{11}$ may be joined to one another in such a way that the radicals $R^{11}$ and the atoms of the cyclopentadienyl ring which correct them form a $C_4-C_{24}$-ring system, which may in turn substituted, l is 5 when v=0, and l is 0.4 when v=1, m is 5 when v=0, and m, is 4 when v=1, $L^1$ may be identical or different and are each a hydrogen atom, a $C_1-C_{10}$-hydrocarbon group such as $C_1-C_{10}$-alkyl or $C_6-C_{10}$-aryl, a halogen atom or $OR^{16}$, $SR^{16}$, $OSi(R^{16})_3$, $Si(R^{16})_3$, $P(R^{16})_2$ or $N(R^{16})_2$, where $R^{16}$ is a halogen atom, a $C_1-C_{10}$-alkyl group, a halogenated $C_1-C_{10}$-alkyl group, a $C_6-C_{20}$-aryl group or a halogenated $C_6-C_{20}$-aryl group, or $L^1$ is a toluenesulfonyl, trifluoroacetyl, trifluoroacetoxyl, trifluoromethanesulfonyl, nonafluorobutanesulfonyl or 2,2,2-trifluoroethanesulfonyl group, o is an integer from 1 to 4, preferably 2, Z is a bridging structural element between the two cyclopentadienyl rings and v is 0 or 1.

Examples of 2 are $M^2R^{13}R^{14}$ groups, where $M^2$ is carbon, silicon, germanium, boron or tin and $R^{13}$ and $R^{14}$ are identical or different and are each a $C_1-C_{20}$-hydrocarbon-containing group such as $C_1-C_{10}$-alkyl, $C_6-C_{14}$-aryl or trimethylsilyl. Z is preferably $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $(C_6H_5)_2Ge$, $(C_6H_5)_2Sn$, $(CH_2)_4Si$, $CH_2Si(CH_3)_2$, o-$C_6H_4$ or 2,2'-$(C_6H_4)_2$; preference is also given to the corresponding compounds having a 1,2-(1-methylethanediyl), 1,2-(1,1-dimethylethanediyl) or 1,2(1,2-dimethylethanediyl) bridge. It is also possible for Z together with one or more radicals $R^{10}$ and/or $R^{11}$ to for, a monocyclic or polycyclic ring system.

Preference is given to chiral bridged metallocene compounds of the formula (II), in particular ones in which v is 1 and one or both cyclopentadienyl rings are substituted so that they form an indenyl ring. The indenyl ring is preferably substituted, in particular in the 2 position, 4 position, 2,4,5 positions, 2,4,6 positions, 2,4,7 positions or 2,4,5,6 positions, by $C_1-C_{20}$ groups, in particular by $C_1-C_{10}$-alkyl or $C_6-C_{20}$-aryl, where two or more substituents of the indenyl ring may also together form a ring system.

Chiral bridged metallocene compounds of the formula (II) can be used as pure racemic or pure meso compounds. However, it is also possible to use mixtures of a racemic compound and a meso compound.

Examples of metallocene compounds are:
dimethylsilanediylbis(indenyl)zirconium dichloride,
dimethylsilanediylbis(4-naphthylindenyl)zirconium dichloride,
dimethylsilanediylbis(2-methylbenzoindenyl)zirconium dichloride,
dimethylsilanediylbis(2-methylindenyl)zirconium dichloride,
dimethylsilanediylbis(2-methyl-4-(1-naphthyl)indenyl)zirconium dichloride,
dimethylsilanediylbis(2-methyl-4-(2-naphthyl)indenyl)zirconium dichloride,
dimethylsilanediylbis(2-methyl-4-phenylindenyl)zirconium dichloride,
dimethylsilanediylbis(2-methyl-4-t-butylindenyl) zirconium dichloride,
dimethylsilanediylbis(2-methyl-4-isopropylindenyl) zirconium dichloride,
dimethylsilanediylbis(2-methyl-4-ethylindenyl)zirconium dichloride,
dimethylsilanediylbis(2-methyl-4-acenaphthylindenyl) zirconium dichloride,
dimethylsilanediylbis(2,4-dimethylindenyl)zirconium chloride,
dimethylsilanediylbis(2-ethylindenyl)zirconium dichloride,
dimethylsilanediylbis(2-ethyl-4-ethylindenyl)zirconium dichloride, dimethylsilanediylbis(2-ethyl-4-phenylindenyl)zirconium dichloride,
dimethylsilanediylbis(2-methyl-4,5-benzoindenyl) zirconium dichloride,
dimethylsilanediylbis(2-methyl-4,6-diisopropylindenyl zirconium dichloride,
dimethylsilanediylbis(2-methyl-4,5-diisopropylindenyl) zirconium dichloride,
dimethylsilanediylbis(2,4,6-trimethylindenyl)zirconium dichloride,
dimethylsilanediylbis(2,5,6-trimethylindenyl)zirconium dichloride,
dimethylsilanediylbis(2,4,7-trimethylindenyl)zirconium dichloride,
dimethylsilanediylbis(2-methyl-5-isobutylindenyl) zirconium dichloride,
dimethylsilanediylbis(2-methyl-5-t-butylindenyl) zirconium dichloride,
methyl(phenyl)silanediylbis(2-methyl-4-phenylindenyl) zirconium dichloride,
methyl(phenyl)silanediylbis(2-methyl-4,6-diisopropylindenyl)zirconium dichloride,
methyl(phenyl)silanediylbis(2-methyl-4-isopropylindenyl) zirconium dichloride,
methyl(phenyl)silanediylbis(2-methyl-4,5-benzoindenyl) zirconium dichloride,
methyl(phenyl)silanediylbis(2-methyl-4,5-(methylbenzo)indenyl)-zirconium dichloride,
methyl(phenyl)silanediylbis(2-methyl-4,5-(tetramethylbenzo)indenyl)-zirconium dichloride,
methyl(phenyl)silanediylbis(2-methyl-4-acenaphthindenyl)-zirconium dichloride,
methyl(phenyl)silanediylbis(2-methyl-indenyl)zirconium dichloride,
methyl(phenyl)silanediylbis(2-methyl-5-isobutylindenyl) zirconium dichloride,
1,2-ethanediylbis(2-methyl-4-phenylindenyl)zirconium dichloride,
1,4-butanediylbis(2-methyl-4-phenylindenyl)zirconium dichloride,
1,2-ethanediylbis(2-methyl-4,6-diisopropylindenyl) zirconium dichloride,
1,4-butanediylbis(2-methyl-4-isopropylindenyl)zirconium dichloride,
1,4-butanediylbis(2-methyl-4,5-benzoindenyl)zirconium dichloride,
1,2-ethanediylbis(2-methyl-4,5-benzoindenyl) zirconium dichloride,
1,2-ethanediylbis(2,4,7-trimethylindenyl)zirconium dichloride,
1,2-ethanediylbis(2-methylindenyl) zirconium dichloride,
1,4-butanediylbis(2-methylindenyl zirconium dichloride,
[4-($\eta^5$-cyclopentadienyl)-4,6,6-trimethyl($\eta^5$-4,5-tetrahydropentalene)]dichlorozirconium,
[4-($\eta^5$-3'-trimethylsilylcyclopentadienyl)-4,6,6-trimethyl($\eta^5$-4,5-tetrahydropentalene)]dichlorozirconium,
[4-($\eta^5$-3'-isopropylcyclopentadienyl)-4,6,6-trimethyl($\eta^5$-4, tetrahydropentalene)]dichlorozirconium,
[4-($\eta^5$-cyclopentadienyl)-4,7,7-trimethyl($\eta^5$-4,5,6,7-tetrahydroindenyl)]dichlorotitanium,
[4-($\eta^5$-cyclopentadienyl)-4,7,7-trimethyl($\eta^5$-4,5,6,7-tetrahydroindenyl)]dichlorozirconium,
[4-($\eta^5$-cyclopentadienyl)-4,7,7-trimethyl($\eta^5$-4,5,6,7-tetrahydroindenyl)]dichlorohafnium,
[4-($\eta^5$-3'-tert-butylcyclopentadienyl)-4,7,7-trimethyl($\eta^5$-4,5,6,7-tetrahydroindenyl)]dichlorotitanium,
4-($\eta^5$-3'-isopropylcyclopentadienyl)-4,7,7-trimethyl($\eta^5$-4,5,6,7-tetrahydroindenyl)]dichlorotitanium,
4-($\eta^5$-3'-methylcyclopentadienyl)-4,7,7-trimethyl($\eta^5$-4,5,6,7-tetrahydroindenyl)]dichlorotitanium,
4-($\eta^5$-3'-trimethylsilylcyclopentadienyl)-2-trimethylsilyl-4,7,7-trimethyl($\eta^5$-4,5,6,7-tetrahydroindenyl)]dichlorotitanium,
4-($\eta^5$-3'-tert-butylcyclopentadienyl)-4,7,7-trimethyl($\eta^5$-4,5,6,7-tetrahydroindenyl)]dichlorozirconium,
(tert-butylamido)(tetramethyl-$\eta^5$-cyclopentadienyl)dimethylsilyl-dichlorotitanium,
(tert-butylamido)(tetramethyl-$\eta^5$-cyclopentadienyl)-1,2-ethanediyldichlorotitanium,
(methylamido)(tetramethyl-$\eta^5$-cyclopentadienyl)dimethylsilyldichlorotitanium,
(methylamido)(tetramethyl-$\eta^5$-cyclopentadienyl)-1,2-ethanediyldichlorotitanium,
(tertbutylamido)-(2,4-dimethyl-2,4-pentadien-1-yl)dimethylsilyldichlorotitanium,
bis(cyclopentadienyl)zirconium dichloride,
bis(n-butylcyclopentadienyl)zirconium dichloride,
bis(1,3-dimethylcyclopentadienyl)zirconium dichloride,
tetrachloro-[1-[bis($\eta^5$-1H-inden-1-ylidene)methylsilyl]-3-$\eta^5$-cyclopenta-2,4-dien-1-ylidene)-3-$\eta^5$-9H-fluoren-9-ylidene)butane]-dizirconium,
tetrachloro-[2-[bis($\eta^5$-2-methyl-1H-inden-1-ylidene)methoxysilyl]-5-($\eta^5$-2,3,4,5-tetramethylcyclopenta-2,4-dien-1-ylidene)-5-($\eta^5$-9H-fluoren-9-ylidene)hexane] dizirconium,
tetrachloro-[1-[bis($\eta^5$-1H-inden-1-ylidene)methylsilyl]-6-($\eta^5$-cyclopenta-2,4-dien-1-ylidene)-6-($\eta^5$-9H-fluoren-9-ylidene)-3-oxaheptane)dizirconium,
dimethylsilanediylbis(2-methyl-4-(tert-butylphenylindenyl)-zirconium dichloride,
dimethylsilanediylbis(2-methyl-4-(4-methylphenylindenyl)-zirconium dichloride,
dimethylsilanediylbis(2-methyl-4-(4-ethylphenylindenyl)-zirconium dichloride,
dimethylsilanediylbis(2-methyl-4-(4-trifluoromethylphenylindenyl)zirconium dichloride,
dimethylsilanediylbis(2-methyl-4-(4-methoxyphenylindenyl)-zirconium dichloride,
dimethylsilanediylbis(2-ethyl-4-(4-tert-butylphenylindenyl)-zirconium dichloride,
dimethylsilanediylbis(2-ethyl-4-(4-methylphenylindenyl) zirconium dichloride,
dimethylsilanediylbis(2-ethyl-4-(4-ethylphenylindenyl) zirconium dichloride,
dimethylsilanediylbis(2-ethyl-4-(4-trifluoromethylphenylindenyl)-zirconium dichloride,
dimethylsilanediylbis(2-ethyl-4-(4-methoxyphenylindenyl)-zirconium dichloride,
dimethylsilanediylbis(2-methyl-4-(4-tert-butylphenylindenyl)-dimethylzirconium,
dimethylsilanediylbis(2-methyl-4-(4-methylphenylindenyl)-dimethylzirconium,
dimethylsilanediylbis(2-methyl-4-(4-ethylphenylindenyl)-dimethylzirconium,
dimethylsilanediylbis(2-methyl-4-(4-trifluoromethylphenyl-indenyl)dimethylzirconium,
dimethylsilanediylbis(2-methyl-4-(4-methoxyphenylindenyl)dimethylzirconium,
dimethylsilanediylbis(2-ethyl-4-(4-tertbutylphenylindenyl)-dimethylzirconium,
dimethylsilanediylbis(2-ethyl-4-(4-methylphenylindenyl) dimethylzirconium,
dimethylsilanediylbis(2-ethyl-4-(4-ethylphenylindenyl) dimethylzirconium,
dimethylsilanediylbis(2-ethyl-4-(4-trifluoromethylphenylindenyl)-dimethylzirconium, dimethylsilanediylbis(2-methyl-4-(4'-methoxyphenylindenyl)dimethylzirconium,
dimethylsilanediylbis(2-methyl-4-(4'-tert-butylphenyl)indenyl)-zirconium dichloride,
dimethylsilanediylbis(2-methyl-4-(4'-tert-butylphenyl)indenyl)-hafnium dichloride,
dimethylsilanediylbis(2-methyl-4-(4'-tert-butylphenyl)indenyl)-titanium dichloride,
dimethylsilanediylbis(2-methyl-4-(4'-methylphenyl)indenyl)-zirconium dichloride,
dimethylsilanediylbis(2-methyl-4-(4'-n-propylphenyl)indenyl)-zirconium dichloride,
dimethylsilanediylbis(2-methyl-4-(4'-n-butylphenyl)indenyl)-zirconium dichloride,
dimethylsilanediylbis(2-methyl-4-(4'-hexylphenyl)indenyl)-zirconium dichloride,
dimethylsilanediylbis(2-methyl-4-(4'-sec-butylphenyl)indenyl)-zirconium dichloride,
dimethylsilanediylbis(2-ethyl-4-phenyl)indenyl)zirconium dichloride,
dimethylsilanediylbis(2-ethyl-4-(4'-methylphenyl)indenyl)-zirconium dichloride,
dimethylsilanediylbis(2-ethyl-4-(4'-ethylphenyl)indenyl)-zirconium dichloride,
dimethylsilanediylbis(2-ethyl-4-(4'-n-propylphenyl)indenyl)-zirconium dichloride,
dimethylsilanediylbis(2-ethyl-4-(4'-n-butylphenyl)indenyl)-zirconium dichloride,
dimethylsilanediylbis(2-ethyl-4-(4'-hexylphenyl)indenyl)-zirconium dichloride,
dimethylsilanediylbis(2-ethyl-4-(4'-pentylphenyl)indenyl)-zirconium dichloride,
dimethylsilanediylbis(2-ethyl-4-(4'-cyclohexylphenyl)indenyl)-zirconium dichloride,
dimethylsilanediylbis(2-ethyl-4-(4'-sec-butylphenyl)indenyl)-zirconium dichloride,
dimethylsilanediylbis(2-ethyl-4-(4'-tert-butylphenyl)indenyl)-zirconium dichloride,
dimethylsilanediylbis(2-n-propyl-4-phenyl)indenyl)zirconium dichloride,
dimethylsilanediylbis(2-n-propyl-4-(4'-methylphenyl)indenyl)-zirconium dichloride,
dimethylsilanediylbis(2-n-propyl-4-(4'-ethylphenyl)indenyl)-zirconium dichloride,
dimethylsilanediylbis(2-n-propyl-4-(4'-isopropylphenyl)indenyl)-zirconium dichloride,
dimethylsilanediylbis(2-n-propyl-4-(4'-n-butylphenyl)indenyl)-zirconium dichloride,
dimethylsilanediylbis(2-n-propyl-4-(4'-hexylphenyl)indenyl)-zirconium dichloride,
dimethylsilanediylbis(2-n-propyl-4-(4'-cyclohexylphenyl)indenyl)-zirconium dichloride,
dimethylsilanediylbis(2-n-propyl-4-(4'-sec-butyl phenyl)indenyl)-zirconium dichloride,
dimethylsilanediylbis(2-n-propyl-4-(4'-tert-butylphenyl)indenyl)-zirconium dichloride,
dimethylsilanediylbis(2-n-butyl-4-phenyl)indenyl)zirconium dichloride,
dimethylsilanediylbis(2-n-butyl-4-(4'-methylphenyl)indenyl)-zirconium dichloride,
dimethylsilanediylbis(2-n-butyl-4-(4'-ethylphenyl)indenyl)-zirconium dichloride,
dimethylsilanediylbis(2-n-butyl-4-(4'-n-propylphenyl)indenyl)-zirconium dichloride,
dimethylsilanediylbis(2-n-butyl-4-(4'-isopropylphenyl)indenyl)-zirconium dichloride,
dimethylsilanediylbis(2-n-butyl-4-(4'-n-butylphenyl)indenyl)-zirconium dichloride,
dimethylsilanediylbis(2-n-butyl-4-(4'-hexylphenyl)indenyl)-zirconium dichloride,
dimethylsilanediylbis(2-n-butyl-4-(4'-cyclohexylphenyl)indenyl)-zirconium dichloride,
dimethylsilanediylbis(2-n-butyl-4-(4'-sec-butylphenyl)indenyl)-zirconium dichloride,
dimethylsilanediylbis(2-n-butyl-4-(4'-tert-butylphenyl)indenyl)-zirconium dichloride,
dimethylsilanediylbis(2-hexyl-4-phenyl)indenyl)zirconium dichloride,
dimethylsilanediylbis(2-hexyl-4-(4'-methylphenyl)indenyl)-zirconium dichloride,
dimethylsilanediylbis(2-hexyl-4-(4'-ethylphenyl)indenyl)-zirconium dichloride,
dimethylsilanediylbis(2-hexyl-4-(4'-n-propylphenyl)indenyl)-zirconium dichloride,
dimethylsilanediylbis(2-hexyl-4-(4'-isopropylphenyl)indenyl)-zirconium dichloride,
dimethylsilanediylbis(2-hexyl-4-(4'-n-butylphenyl)indenyl)-zirconium dichloride,
dimethylsilanediylbis(2-hexyl-4-(4'-hexylphenyl)indenyl)-zirconium dichloride,
dimethylsilanediylbis(2-hexyl-4-(4'-cyclohexylphenyl)indenyl)-zirconium dichloride,
dimethylsilanediylbis(2-hexyl-4-(4'-sec-butylphenyl)indenyl)-zirconium dichloride,
dimethylsilanediylbis(2-hexyl-4-(4'-tert-butylphenyl)indenyl)-zirconium dichloride,
dimethylsilanediylbis(2-methyl-4-(4'-tert-butylphenyl)indenyl)-zirconium bis(dimethylamide),
dimethylsilanediylbis(2-ethyl-4-(4'-tert-butylphenyl)indenyl)-dibenzylzirconium,
dimethylsilanediylbis(2-methyl-4-(4'-tert-butylphenyl)indenyl)-dimethylzirconium,
dimethylgermanediylbis(2-ethyl-4-(4'-tert-butylphenyl)indenyl)-zirconium dichloride,
dimethylgermanediylbis(2-ethyl-4-(4'-tert-butylphenyl)indenyl)-hafnium dichloride,
dimethylgermanediylbis(2-propyl-4-(4'-tert-butylphenyl)indenyl)-titanium dichloride,
dimethylgermanediylbis(2-methyl-4-(4'-tert-butylphenyl)indenyl)-zirconium dichloride,
ethylidenebis(2-ethyl-4-phenyl)indenyl)zirconium dichloride,
ethylidenebis(2-ethyl-4-(4'-tert-butylphenyl)indenyl) zirconium dichloride,
ethylidenebis(2-n-propyl-4-(4'-tert-butylphenyl)indenyl)-zirconium dichloride,
ethylidenebis(2-n-butyl-4-(4'-tert-butylphenyl)indenyl) titanium dichloride,
ethylidenebis(2-hexyl-4-(4'-tert-butylphenyl)indenyl) dibenzyl-zirconium,
ethylidenebis(2-ethyl-4-(4'-tert-butylphenyl)indenyl) dibenzyl-hafnium,
ethylidenebis(2-methyl-4-(4'-tert-butylphenyl)indenyl) dibenzyl-titanium,
ethylidenebis(2-methyl-4-(4'-tert-butylphenyl)indenyl) zirconium dichloride,
ethylidenebis(2-ethyl-4-(4'-tert-butylphenyl)indenyl) dimethyl-hafnium,
ethylidenebis(2-n-propyl-4-phenyl)indenyl) dimethyltitanium,
ethylidenebis(2-ethyl-4-(4'-tert-butylphenyl)indenyl) zirconium bis(dimethylamide),
ethylidenebis(2-ethyl-4-(4'-tert-butylphenyl)indenyl) hafnium bis(dimethylamide),
ethylidenebis(2-ethyl-4-(4'-tert-butylphenyl)indenyl) titanium bis(dimethylamide), methylethylidenebis(2-ethyl-4-(4'-tert-butylphenyl) indenyl)-zirconium dichloride,
methylethylidenebis(2-ethyl-4-(4'-tert-butylphenyl) indenyl)-hafnium dichloride,
phenylphosphinediyl(2-ethyl-4-(4'-tert-butylphenyl) indenyl)-zirconium dichloride,
phenylphosphinediyl(2-methyl-4-(4'-tert-butylphenyl) indenyl)-zirconium dichloride,
phenylphosphinediyl(2-ethyl-4-(4'-tert-butylphenyl) indenyl)-zirconium dichloride,
dimethylsilanediyl(2-methyl-4-azapentalene)(2-methyl-4-(4'-methylphenylindenyl)zirconium dichloride,
dimethylsilanediyl(2-methyl-5-azapentalene)(2-ethyl-4-(4'-methylphenylindenyl)zirconium dichloride,
dimethylsilanediyl(2-methyl-6-azapentalene)(2-methyl-4-(4'-methylphenylindenyl)zirconium dichloride,
dimethylsilanediyl(2-methyl-N-phenyl-4-azapentalene)(2-methyl-4-(4'-methylphenylindenyl)zirconium dichloride,
dimethylsilanediyl(2-methyl-N-phenyl-5-azapentalene)(2-methyl-4-(4'-methylphenylindenyl)zirconium dichloride,
dimethylsilanediyl(2-methyl-N-phenyl-6-azapentalene)(2-methyl-4-(4'-methylphenylindenyl)zirconium dichloride,
dimethylsilanediyl(2,5-dimethyl-4-azapentalene)(2-methyl-4-(4'-methylphenylindenyl)zirconium dichloride,
dimethylsilanediyl(2,5-dimethyl-6-azapentalene)(2-methyl-4-(4'-methylphenylindenyl)zirconium dichloride,
dimethylsilanediyl(2,5-dimethyl-N-phenyl-4-azapentalene)(2-methyl-4-(4-methylphenylindenyl)zirconium dichloride,
dimethylsilanediyl(2,5-dimethyl-N-phenyl-6-azapentalene)(2-methyl-4-(4'-methylphenylindenyl)zirconium dichloride,
dimethylsilanediyl(2-methyl-4-thiapentalene)(2-methyl-4-(4'-methylphenylindenyl)zirconium dichloride,
dimethylsilanediyl(2-methyl-5-thiapentalene)(2-methyl-4-(4'-methylphenylindenyl)zirconium dichloride,
dimethylsilanediyl(2-methyl-6-thiapentalene)(2-methyl-4-(4'-methylphenylindenyl)zirconium dichloride,
dimethylsilanediyl(2,5-dimethyl-4-thiapentalene)(2-methyl-4-(4'-methylphenylindenyl)zirconium dichloride,
dimethylsilanediyl(2,5-dimethyl-6-thiapentalene)(2-methyl-4-(4'-methylphenylindenyl)zirconium dichloride,
dimethylsilanediyl(2-methyl-4-oxapentalene(2-2methyl-4-(4'-methylphenylindenyl)zirconium dichloride,
dimethylsilanediyl(2-methyl-5-oxapentalene)(2-methyl-4-(4'-methylphenylindenyl)zirconium dichloride,
dimethylsilanediyl(2-methyl-6-oxapentalene)(2-methyl-4-(4'-methylphenylindenyl)zirconium dichloride,
dimethylsilanediyl(2,5-dimethyl-4-oxapentalene)(2-methyl-4-(4'-methylphenylindenyl)zirconium dichloride,
dimethylsilanediyl(2,5-dimethyl-6-oxapentalene)(2-methyl-4-(4'methylphenylindenyl)zirconium dichloride,
dimethylsilanediyl(2-methyl-4-azapentalene)(2-methyl-4-(4'-ethylphenylindenyl)zirconium dichloride,
dimethylsilanediyl(2-methyl-5-azapentalene)(2-methyl-4-(4'-methylphenylindenyl)zirconium dichloride,
dimethylsilanediyl(2-methyl-6-azapentalene)(2-methyl-4-(4'-ethylphenylindenyl)zirconium dichloride,
dimethylsilanediyl(2-methyl-N-phenyl-4-azapentalene)(2-methyl-4-(4'-ethylphenylindenyl)zirconium dichloride,
dimethylsilanediyl(2-methyl-N-phenyl-5-azapentalene)(2-methyl-4-(4'-ethylphenylindenyl)zirconium dichloride,
dimethylsilanediyl(2-methyl-N-phenyl-6-azapentalene)(2-methyl-4-(4'-ethylphenylindenyl)zirconium dichloride,
dimethylsilanediyl(2,5-dimethyl-4-azapentalene)(2-methyl-4-(4'-ethylphenylindenyl)zirconium dichloride,
dimethylsilanediyl(2,5-dimethyl-6-azapentalene)(2-methyl-4-(4'-ethylphenylindenyl)zirconium dichloride,
dimethylsilanediyl(2,5-dimethyl-N-phenyl-4-azapentalene)(2-methyl-4-(4'-ethylphenylindenyl)zirconium dichloride,
dimethylsilanediyl(2,5-dimethyl-N-phenyl-6-azapentalene)(2-methyl-4-(4'-ethylphenylindenyl)zirconium dichloride,
dimethylsilanediyl(2-methyl-4-thiapentalene)(2-methyl-4-(4'-ethylphenylindenyl)zirconium dichloride,
dimethylsilanediyl(2-methyl-5-thiapentalene)(2-methyl-4-(4'-ethylphenylindenyl)zirconium dichloride,
dimethylsilanediyl(2-methyl-6-thiapentalene)(2-methyl-4-(4'ethylphenylindenyl)zirconium dichloride,
dimethylsilanediyl(2,5-dimethyl-4-thiapentalene)(2-methyl-4-(4'-ethylphenylindenyl)zirconium dichloride,
dimethylsilanediyl(2,5-dimethyl-6-thiapentalene)(2-methyl-4-(4'-ethylphenylindenyl)zirconium dichloride,
dimethylsilanediyl(2-methyl-4-oxapentalene)(2-methyl-4-(4'-ethylphenylindenyl)zirconium dichloride,
dimethylsilanediyl(2-methyl-5-oxapentalene)(2-methyl-4-(4'-ethylphenylindenyl)zirconium dichloride,
dimethylsilanediyl(2-methyl-6-oxapentalene)(2-methyl-4-(4'-ethylphenylindenyl)zirconium dichloride,
dimethylsilanediyl(2,5-dimethyl-4-oxapentalene)(2-methyl-4-(4'-ethylphenylindenyl)zirconium dichloride,
dimethylsilanediyl(2,5-dimethyl-6-oxapentalene)(2-methyl-4-(4'-ethylphenylindenyl)zirconium dichloride,
dimethylsilanediyl(2-methyl-4-azapentalene)(2-methyl-4-(4'-n-propylphenylindenyl)zirconium dichloride,
dimethylsilanediyl(2-methyl-5-azapentalene)(2-methyl-4-(4'-n-propylphenylindenyl)zirconium dichloride,
dimethylsilanediyl(2-methyl-6-azapentalene)(2-methyl-4-(4'-n-propylphenylindenyl)zirconium dichloride,
dimethylsilanediyl(2-methyl-N-phenyl-4-azapentalene)(2-methyl-4-(4'-n-propylphenylindenyl)zirconium dichloride,
dimethylsilanediyl(2-methyl-N-phenyl-5-azapentalene)(2-methyl-4-(4'-n-propylphenylindenyl)zirconium dichloride,
dimethylsilanediyl(2-methyl-N-phenyl-6-azapentalene)(2-methyl-4(4'-n-propylphenylindenyl)zirconium dichloride,
dimethylsilanediyl(2,5-dimethyl-4-azapentalene)(2-methyl-4-(4'-n-propylphenylindenyl)zirconium dichloride,
dimethylsilanediyl(25-dimethyl-6-azapentalene)(2-methyl-4-(4'-n-propylphenylindenyl)zirconium dichloride,
dimethylsilanediyl(2,5-dimethyl-N-phenyl-4-azapentalene)(2-methyl-4-(4'-n-propylphenylindenyl)zirconium dichloride,
dimethylsilanediyl(2,5-dimethyl-N-phenyl-6-azapentalene)(2-methyl-4-(4'-n-propylphenylindenyl)zirconium dichloride,
dimethylsilanediyl(2-methyl-4-thiapentalene)(2-methyl-4-(4'-n-propylphenylindenyl)zirconium dichloride,
dimethylsilanediyl(2-methyl-5-thiapentalene)(2-methyl-4-(4'-n-propylphenylindenyl)zirconium dichloride,
dimethylsilanediyl(2-methyl-6-thiapentalene)(2-methyl-4-(4'-n-propylphenylindenyl)zirconium dichloride,
dimethylsilanediyl(2,5-dimethyl-4-thiapentalene)(2-methyl-4-(4'-n-propylphenylindenyl)zirconium dichloride,
dimethylsilanediyl(2,5-dimethyl-6-thiapentalene)(2-methyl-4-(4'-n-propylphenylindenyl)zirconium dichloride,
dimethylsilanediyl(2-methyl-4-oxapentalene)(2-methyl-4-(4'-n-propylphenylindenyl)zirconium dichloride,
dimethylsilanediyl(2-methyl-5-oxapentalene)(2-methyl-4-(4'-n-propylphenylindenyl)zirconium dichloride, dimethylsilanediyl(2-methyl-6-oxapentalene)(2-methyl-4-(4'-n-propylphenylindenyl)zirconium dichloride,
dimethylsilanediyl(2,5-dimethyl-4-oxapentalene)(2-methyl-4-(4'-n-propylphenylindenyl)zirconium dichloride,
dimethylsilanediyl(2,5-dimethyl-6-oxapentalene)(2-methyl-4-(4'-n-propylphenylindenyl)zirconium dichloride,
dimethylsilanediyl(2-methyl-4-azapentalene)(2-methyl-4-(4'-isopropylphenylindenyl)zirconium dichloride,
dimethylsilanediyl(2-methyl-5-azapentalene)(2-methyl-4-(4'-isopropylphenylindenyl)zirconium dichloride,
dimethylsilanediyl(2-methyl-6-azapentalene)(2-methyl-4-(4'-isopropylphenylindenyl)zirconium dichloride,
dimethylsilanediyl(2-methyl-N-phenyl-4-azapentalene)(2-methyl-4-(4'-isopropylphenylindenyl)zirconium dichloride,
dimethylsilanediyl(2-methyl-N-phenyl-5-azapentalene)(2-methyl-4-(4'-isopropylphenylindenyl)zirconium dichloride,
dimethylsilanediyl(2-methyl-N-phenyl-6-azapentalene))(2-methyl-4-(4'-isopropylphenylindenyl)zirconium dichloride,
dimethylsilanediyl(2,5-dimethyl-4-azapentalene)(2-methyl-4-(4'-isopropylphenylindenyl)zirconium dichloride,
dimethylsilanediyl(2,5-dimethyl-6-azapentalene)(2-methyl-4-(4'-isopropylphenylindenyl)zirconium dichloride,
dimethylsilanediyl(2,5-dimethyl-N-phenyl-4-azapentalene)(2-methyl-4-(4'-isopropylphenylindenyl)zirconium dichloride,
dimethylsilanediyl(2,5-dimethyl-N-phenyl-6-azapentalene)(2-methyl-4-(4'-isopropylphenylindenyl)zirconium dichloride,
dimethylsilanediyl(2-methyl-4-thiapentalene)(2-methyl-4-(4'-isopropylphenylindenyl)zirconium dichloride,
dimethylsilanediyl(2-methyl-5-thiapentalene)(2-methyl-4-(4'-isopropylphenylindenyl)zirconium dichloride,
dimethylsilanediyl(2-methyl-4-(4'-isopropylphenylindenyl)zirconium dichloride,
dimethylsilanediyl(2,5-dimethyl-4-thiapentalene)(2-methyl-4-(4'-isopropylphenylindenyl)zirconium dichloride,
dimethylsilanediyl(2,5-dimethyl-6-thiapentalene)(2-methyl-4-(4'-isopropylphenylindenyl)zirconium dichloride,
dimethylsilanediyl(2-methyl-4-oxapentalene)(2-methyl-4-(4'-isopropylphenylindenyl)zirconium dichloride,
dimethylsilanediyl(2-methyl-5-oxapentalene)(2-methyl-4-(4'-isopropylphenylindenyl)zirconium dichloride,
dimethylsilanediyl(2-methyl-6-oxapentalene)(2-methyl-4-(4'-isopropylphenylindenyl)zirconium dichloride,
dimethylsilanediyl(2,5-dimethyl-4-oxapentalene)(2-methyl-4-(4'-isopropylphenylindenyl)zirconium dichloride,
dimethylsilanediyl(2,5-dimethyl-6-oxapentalene)(2-methyl-4-(4'-isopropylphenylindenyl)zirconium dichloride,
dimethylsilanediyl(2-methyl-4-azapentalene)(2-methyl-4-(4'-n-butylphenylindenyl)zirconium dichloride,
dimethylsilanediyl(2-methyl-5-azapentalene)(2-methyl-4-(4'-n-butylphenylindenyl)zirconium dichloride,
dimethylsilanediyl(2-methyl-6-azapentalene)(2-methyl-4-(4'-n-butylphenylindenyl)zirconium dichloride,
dimethylsilanediyl(2-methyl-N-phenyl-4-azapentalene)(2-methyl-4-(4'-n-butylphenylindenyl)zirconium dichloride,
dimethylsilanediyl(2-methyl-N-phenyl-5-azapentalene)(2-methyl-4-(4'-n-butylphenylindenyl)zirconium dichloride,
dimethylsilanediyl(2-methyl-N-phenyl-6-azapentalene)(2-methyl-4-(4'-n-butylphenylindenyl)zirconium dichloride,
dimethylsilanediyl(2,5-dimethyl-4-azapentalene)(2-methyl-4-(4'-n-butylphenylindenyl)zirconium dichloride,
dimethylsilanediyl(2,5-dimethyl-6-azapentalene)(2-methyl-4-(4'-n-butylphenylindenyl)zirconium dichloride,
dimethylsilanediyl(2,5-dimethyl-N-phenyl-4-azapentalene)(2-methyl-4-(4'-n-butylphenylindenyl)zirconium dichloride,
dimethylsilanediyl(2,5-dimethyl-N-phenyl-6-azapentalene)(2-methyl-4-(4'-n-butylphenylindenyl)zirconium dichloride,
dimethylsilanediyl(2-methyl-4-thiapentalene)(2-methyl-4-(4'-n-butylphenylindenyl)zirconium dichloride,
dimethylsilanediyl(2-methyl-5-thiapentalene)(2-methyl-4-(4'-n-butylphenylindenyl)zirconium dichloride,
dimethylsilanediyl(2-methyl-6-thiapentalene)(2-methyl-4-(4'-n-butylphenylindenyl)zirconium dichloride,
dimethylsilanediyl(2,5-dimethyl-4-thiapentalene)(2-methyl-4-(4'-n-butylphenylindenyl)zirconium dichloride,
dimethylsilanediyl(2,5-dimethyl-6-thiapentalene)(2-methyl-4-(4'-n-butylphenylindenyl)zirconium dichloride,
dimethylsilanediyl(2-methyl-4-oxapentalene)(2-methyl-4-(4'-n-butylphenylindenyl)zirconium dichloride,
dimethylsilanediyl(2-methyl-5-oxapentalene)(2-methyl-4-(4'-n-butylphenylindenyl)zirconium dichloride,
dimethylsilanediyl(2-methyl-6-oxapentalene)(2-methyl-4-(4'-n-butylphenylindenyl)zirconium dichloride,
dimethylsilanediyl(2,5-dimethyl-4-oxapentalene)(2-methyl-4-(4'-n-butylphenylindenyl)zirconium dichloride,
dimethylsilanediyl(2,5-dimethyl-6-oxapentalene)(2-methyl-4-(4'-n-butylphenylindenyl)zirconium dichloride,
dimethylsilanediyl(2-methyl-4-azapentalene)(2-methyl-4-(4'-s-butylphenylindenyl)zirconium dichloride,
dimethylsilanediyl(2-methyl-5-azapentalene)(2-methyl-4-(4'-s-butylphenylindenyl)zirconium dichloride,
dimethylsilanediyl(2-methyl-6-azapentalene)(2-methyl-4-(4'-s-butylphenylindenyl)zirconium dichloride,
dimethylsilanediyl(2-methyl-N-phenyl-4-azapentalene)(2-methyl-4-(4'-s-butylphenylindenyl)zirconium dichloride,
dimethylsilanediyl(2-methyl-N-phenyl-5-azapentalene)(2-methyl-4-(4'-s-butylphenylindenyl)zirconium dichloride,
dimethylsilanediyl(2-methyl-N-phenyl-6-azapentalene)(2-methyl-4-(4'-s-butylphenylindenyl)zirconium dichloride,
dimethylsilanediyl(2,5-dimethyl-4-azapentalene)(2-methyl-4-(4'-s-butylphenylindenyl)zirconium dichloride,
dimethylsilanediyl(2,5-dimethyl-6-azapentalene)(2-methyl-4-(4'-s-butylphenylindenyl)zirconium dichloride,
dimethylsilanediyl(2,5-dimethyl-N-phenyl-4-azapentalene)(2-methyl-4-(4'-s-butylphenylindenyl)zirconium dichloride,
dimethylsilanediyl(2,5-dimethyl-N-phenyl-6-azapentalene)(2-methyl-4-(4'-s-butylphenylindenyl)zirconium dichloride,
dimethylsilanediyl(2-methyl-4-thiapentalene)(2-methyl-4-(4'-s-butylphenylindenyl)zirconium dichloride,
dimethylsilanediyl(2-methyl-5-thiapentalene)(2-methyl-4-(4'-s-butylphenylindenyl)zirconium dichloride,
dimethylsilanediyl(2-methyl-6-thiapentalene)(2-methyl-4-(4'-s-butylphenylindenyl)zirconium dichloride,
dimethylsilanediyl(2,5-dimethyl-4-thiapentalene)(2-methyl-4-(4'-s-butylphenylindenyl)zirconium dichloride,
dimethylsilanediyl(2,5-dimethyl-6-thiapentalene)(2-methyl-4-(4'-s-butylphenylindenyl)zirconium dichloride,
dimethylsilanediyl(2-methyl-4-oxapentalene)(2-methyl-4-(4'-s-butylphenylindenyl)zirconium dichloride,
dimethylsilanediyl(2-methyl-5-oxapentalene)(2-methyl-4-(4'-s-butylphenylindenyl)zirconium dichloride,
dimethylsilanediyl(2-methyl-6-oxapentalene)(2-methyl-4-(4'-s-butylphenylindenyl)zirconium dichloride,
dimethylsilanediyl(2,5-dimethyl-4-oxapentalene)(2-methyl-4-(4's-butylphenylindenyl)zirconium dichloride, dimethylsilanediyl(2,5-dimethyl-6-oxapentalene)(2-methyl-4-(4'-s-butylphenylindenyl)zirconium dichloride,
dimethylsilanediyl(2-methyl-4-azapentalene)(2-methyl-4-(4'-tert-butylphenylindenyl)zirconium dichloride,
dimethylsilanediyl(2-methyl-5-azapentalene)(2-methyl-4-(4'-tert-butylphenylindenyl)zirconium dichloride,
dimethylsilanediyl(2-methyl-6-azapentalene)(2-methyl-4-(4'-tert-butylphenylindenyl)zirconium dichloride,
dimethylsilanediyl(2-methyl-N-phenyl-4-azapentalene)(2-methyl-4-(4'-tert-butylphenylindenyl)zirconium dichloride,
dimethylsilanediyl(2-methyl-N-phenyl-5-azapentalene)(2-methyl-4-(4'-tert-butylphenylindenyl)zirconium dichloride,
dimethylsilanediyl(2-methyl-N-phenyl-6-azapentalene)(2-methyl-4-(4'-tert-butylphenylindenyl)zirconium dichloride,
dimethylsilanediyl(2,5-dimethyl-4-azapentalene)(2-methyl-4-(4'-tert-butylphenylindenyl)zirconium dichloride,
dimethylsilanediyl(2,5-dimethyl-6-azapentalene)(2-methyl-4(4'-tert-butylphenylindenyl)zirconium dichloride,
dimethylsilanediyl(2,5-dimethyl-N-phenyl-4-azapentalene)(2-methyl-4-(4'-tert-butylphenylindenyl)zirconium dichloride,
dimethylsilanediyl 2,5-dimethyl-N-phenyl-6-azapentalene)(2-methyl-4-(4'-tert-butylphenylindenyl)zirconium dichloride,
dimethylsilanediyl(2-methyl-4-thiapentalene)(2-methyl-4-(4'-tert-butylphenylindenyl)zirconium dichloride,
dimethylsilanediyl(2-methyl-5-thiapentalene)(2-methyl-4-(4'-tert-butylphenylindenyl)zirconium dichloride,
dimethylsilanediyl(2-methyl-6-thiapentalene)(2-methyl-4-(4'-tert-butylphenylindenyl)zirconium dichloride,
dimethylsilanediyl(2,5-dimethyl-4-thiapentalene)(2-methyl-4-(4'-tert-butylphenylindenyl)zirconium dichloride,
dimethylsilanediyl(2,5-dimethyl-6-thiapentalene)(2-methyl-4-(4'-tert-butylphenylindenyl)zirconium dichloride,
dimethylsilanediyl(2-methyl-4-oxapentalene)(2-methyl-4-(4'-tert-butylphenylindenyl)zirconium dichloride,
dimethylsilanediyl(2-methyl-5-oxapentalene)(2-methyl-4-(4'-tert-butylphenylindenyl)zirconium dichloride,
dimethylsilanediyl(2-methyl-6-oxapentalene)(2-methyl-4-(4'-tert-butylphenylindenyl)zirconium dichloride,
dimethylsilanediyl(2,5-dimethyl-4-oxapentalene)(2-methyl-4-(4'-tert-butylphenylindenyl)zirconium dichloride,
dimethylsilanediyl(2,5-dimethyl-6-oxapentalene)(2-methyl-4-(4'-tert-butylphenylindenyl)zirconium dichloride,
dimethylsilanediyl(2-methyl-4-azapentalene)(2-methyl-4-(4'-n-pentylphenylindenyl)zirconium dichloride,
dimethylsilanediyl(2-methyl-5-azapentalene)(2-methyl-4-(4'-n-pentylphenylindenyl)zirconium dichloride,
dimethylsilanediyl(2-methyl-6-azapentalene)(2-methyl-4-(4'-n-pentylphenylindenyl)zirconium dichloride,
dimethylsilanediyl(2-methyl-N-phenyl-4-azapentalene)(2-methyl-4-(4'-n-pentylphenylindenyl)zirconium dichloride,
dimethylsilanediyl(2-methyl-N-phenyl-5-azapentalene)(2-methyl-4-(4'-n-pentylphenylindenyl)zirconium dichloride,
dimethylsilanediyl(2-methyl-N-phenyl-6-azapentalene)(2-methyl-4-(4'-n-pentylphenylindenyl)zirconium dichloride,
dimethylsilanediyl(2,5-dimethyl-4-azapentalene)(2-methyl-4-(4'-n-pentylphenylindenyl)zirconium dichloride,
dimethylsilanediyl(2,5-dimethyl-6-azapentalene)(2-methyl-4-(4'-n-pentylphenylindenyl)zirconium dichloride,
dimethylsilanediyl(2,5-dimethyl-N-phenyl-4-azapentalene)(2-methyl-4-(4'-n-pentylphenylindenyl)zirconium dichloride,
dimethylsilanediyl(2,5-dimethyl-N-phenyl-6-azapentalene)(2-methyl-4-(4'-n-pentylphenylindenyl)zirconium dichloride,
dimethylsilanediyl(2-methyl-4-thiapentalene)(2-methyl-4-(4'-n-pentylphenylindenyl)zirconium dichloride,
dimethylsilanediyl(2-methyl-5-thiapentalene)(2-methyl-4-(4'-n-pentylphenylindenyl)zirconium dichloride,
dimethylsilanediyl(2-methyl-6-thiapentalene)(2-methyl-4-(4'-n-pentylphenylindenyl)zirconium dichloride,
dimethylsilanediyl(2,5-dimethyl-4-thiapentalene)(2-methyl-4-(4'-n-pentylphenylindenyl)zirconium dichloride,
dimethylsilanediyl(2,5-dimethyl-6-thiapentalene)(2-methyl-4-(4'-n-pentylphenylindenyl)zirconium dichloride,
dimethylsilanediyl(2-methyl-4-oxapentalene)(2-methyl-4-(4'-n-pentylphenylindenyl)zirconium dichloride,
dimethylsilanediyl(2-ethyl-5-oxapentalene)(2-methyl-4-(4'-n-pentylphenylindenyl)zirconium dichloride,
dimethylsilanediyl(2-methyl-6-oxapentalene)(2-methyl-4-(4'-n-pentylphenylindenyl)zirconium dichloride,
dimethylsilanediyl(2,5-dimethyl-4-oxapentalene)(2-methyl-4-(4'-n-pentylphenylindenyl)zirconium dichloride,
dimethylsilanediyl(2,5-dimethyl-6-oxapentalene)(2-methyl-4-(4'-n-pentylphenylindenyl)zirconium dichloride,
dimethylsilanediyl(2-methyl-4-azapentalene)(2-methyl-4-(4'-n-hexylphenylindenyl)zirconium dichloride,
dimethylsilanediyl(2-methyl-5-azapentalene)(2-methyl-4-(4'-n-hexylphenylindenyl)zirconium dichloride,
dimethylsilanediyl(2-methyl-4-(4'-n-hexylphenylindenyl)zirconium dichloride,
dimethylsilanediyl(2-methyl-N-phenyl-4-azapentalene)(2-methyl-4-(4'-n-hexylphenylindenyl)zirconium dichloride,
dimethylsilanediyl(2-methyl-N-phenyl-5-azapentalene)(2-methyl-4-(4'-n-hexylphenylindenyl)zirconium dichloride,
dimethylsilanediyl(2-methyl-N-phenyl-6-azapentalene)(2-methyl-4-(4'-n-hexylphenylindenyl)zirconium dichloride,
dimethylsilanediyl(2,5-dimethyl-4-azapentalene)(2-methyl-4-(4'-n-hexylphenylindenyl)zirconium dichloride,
dimethylsilanediyl(2,5-dimethyl-6-azapentalene)(2-methyl-4-(4'-n-hexylphenylindenyl)zirconium dichloride,
dimethylsilanediyl(2,5-dimethyl-N-phenyl-4-azapentalene)(2-methyl-4-(4'-n-hexylphenylindenyl)zirconium dichloride,
dimethylsilanediyl(2,5-dimethyl-N-phenyl-6-azapentalene)(2-methyl-4-(4'-n-hexylphenylindenyl)zirconium dichloride,
dimethylsilanediyl(2-methyl-4-thiapentalene)(2-methyl-4-(4'-n-hexylphenylindenyl)zirconium dichloride,
dimethylsilanediyl(2-methyl-5-thiapentalene)(2-methyl-4-(4'-n-hexylphenylindenyl)zirconium dichloride,
dimethylsilanediyl(2-methyl-6-thiapentalene)(2-methyl-4-(4'-n-hexylphenylindenyl)zirconium dichloride,
dimethylsilanediyl(2,5-dimethyl-4-thiapentalene)(2-methyl-4-(4'-n-hexylphenylindenyl)zirconium dichloride,
dimethylsilanediyl(2,5-dimethyl-6-thiapentalene)(2-methyl-4-(4'-n-hexylphenylindenyl)zirconium dichloride,
dimethylsilanediyl(2-methyl-4-oxapentalene)(2-methyl-4-(4'-n-hexylphenylindenyl)zirconium dichloride,
dimethylsilanediyl(2-methyl-5-oxapentalene)(2-methyl-4-(4'-n-hexylphenylindenyl)zirconium dichloride,
dimethylsilanediyl(2-methyl-6-oxapentalene)(2-methyl-4-(4'-n-hexylphenylindenyl)zirconium dichloride,
dimethylsilanediyl(2,5-dimethyl-4-oxapentalene)(2-methyl-4-(4'-n-hexylphenylindenyl)zirconium dichloride, dimethylsilanediyl(2,5-dimethyl-6-oxapentalene)(2-methyl-4-(4'-n-hexylphenylindenyl)zirconium dichloride,
dimethylsilanediyl(2-methyl-4-azapentalene)(2-methyl-4-(4'-cyclohexylphenylindenyl)zirconium dichloride,
dimethylsilanediyl(2-methyl-5-azapentalene)(2-methyl-4-(4'-cyclohexylphenylindenyl)zirconium dichloride,
dimethylsilanediyl(2-methyl-6-azapentalene)(2-methyl-4-(4'-cyclohexylphenylindenyl)zirconium dichloride,
dimethylsilanediyl(2-methyl-N-phenyl-4-azapentalene)(2-methyl-4-(4'-cyclohexylphenylindenyl)zirconium dichloride,
dimethylsilanediyl(2-methyl-N-phenyl-5-azapentalene)(2-methyl-4-(4'-cyclohexylphenylindenyl)zirconium dichloride,
dimethylsilanediyl(2-methyl-N-phenyl-6-azapentalene)(2-methyl-4-(4'-cyclohexylphenylindenyl)zirconium dichloride,
dimethylsilanediyl(2,5-dimethyl-4-azapentalene)(2-methyl-4-(4'-cyclohexylphenylindenyl)zirconium dichloride,
dimethylsilanediyl(2,5-dimethyl-6-azapentalene)(2-methyl-4-(4'-cyclohexylphenylindenyl)zirconium dichloride,
dimethylsilanediyl(2,5-dimethyl-N-phenyl-4-azapentalene)(2-methyl-4-(4-cyclohexylphenylindenyl)zirconium dichloride,
dimethylsilanediyl(2,5-dimethyl-N-phenyl-6-azapentalene)(2-methyl-4-(4'-cyclohexylphenylindenyl)zirconium dichloride,
dimethylsilanediyl(2-methyl-4-thiapentalene)(2-methyl-4-(4'-cyclohexylphenylindenyl)zirconium dichloride,
dimethylsilanediyl(2-methyl-5-thiapentalene)(2-methyl-4-(4'-cyclohexylphenylindenyl)zirconium dichloride,
dimethylsilanediyl(2-methyl-6-thiapentalene)(2-methyl-4-(4'-cyclohexylphenylindenyl)zirconium dichloride,
dimethylsilanediyl(2,5-dimethyl-4-thiapentalene)(2-methyl-4-(4'-cyclohexylphenylindenyl)zirconium dichloride,
dimethylsilanediyl(2,5-dimethyl-6-thiapentalene)(2-methyl-4-(4'-cyclohexylphenylindenyl)zirconium dichloride,
dimethylsilanediyl(2-methyl-4-oxapentalene) (2methyl-4-(4'-cyclohexylphenylindenyl)zirconium dichloride,
dimethylsilanediyl(2-methyl-5-oxapentalene)(2-methyl-4-(4'-cyclohexylphenylindenyl)zirconium dichloride,
dimethylsilanediyl(2-methyl-6-oxapentalene)(2-methyl-4-(4'-cyclohexylphenylindenyl)zirconium dichloride,
dimethylsilanediyl(2,5-dimethyl-4-oxapentalene)(2-methyl-4-(4'-cyclohexylphenylindenyl)zirconium dichloride,
dimethylsilanediyl(2,5-dimethyl-6-oxapentalene)(2-methyl-4-(4'-cyclohexylphenylindenyl)zirconium dichloride,
dimethylsilanediyl(2-methyl-4-azapentalene) 2-methyl-4-(4'-trimethylsilylphenylindenyl)zirconium dichloride,
dimethylsilanediyl(2-methyl-5-azapentalene)(2-methyl-4-(4'-trimethylsilylphenylindenyl)zirconium dichloride,
dimethylsilanediyl(2-methyl-6-azapentalene)(2-methyl-4-(4'-trimethylsilylphenylindenyl)zirconium dichloride,
dimethylsilanediyl(2-methyl-N-phenyl-4-azapentalene)(2-methyl-4-(4'-trimethylsilylphenylindenyl)zirconium dichloride,
dimethylsilanediyl(2-methyl-N-phenyl-5-azapentalene)(2-methyl-4-(4'-trimethylsilylphenylindenyl)zirconium dichloride,
dimethylsilanediyl(2-methyl-N-phenyl-6-azapentalene)(2-methyl-4-(4'-trimethylsilylphenylindenyl)zirconium dichloride,
dimethylsilanediyl(2,5-dimethyl-4-azapentalene)(2-methyl-4-(4'-trimethylsilylphenylindenyl)zirconium dichloride,
dimethylsilanediyl(2,5-dimethyl-6-azapentalene)(2-methyl-4-(4'-trimethylsilylphenylindenyl)zirconium dichloride,
dimethylsilanediyl(2,5-dimethyl-N-phenyl-4-azapentalene)(2-methyl-4-(4'-trimethylsilylphenylindenyl)zirconium dichloride,
dimethylsilanediyl(2,5-dimethyl-N-phenyl-6-azapentalene)(2-methyl-4-(4'-trimethylsilylphenylindenyl)zirconium dichloride,
dimethylsilanediyl(2-methyl-4-thiapentalene)(2-methyl-4-(4'-trimethylsilylphenylindenyl)zirconium dichloride,
dimethylsilanediyl(2-methyl-5-thiapentalene)(2-methyl-4-(4'-trimethylsilylphenylindenyl)zirconium dichloride,
dimethylsilanediyl(2-methyl-6-thiapentalene)(2-methyl-4-(4'-trimethylsilylphenylindenyl)zirconium dichloride,
dimethylsilanediyl(2,5-dimethyl-4-thiapentalene)(2-methyl-4-(4'-trimethylsilylphenylindenyl)zirconium dichloride,
dimethylsilanediyl(2,5-dimethyl-6-thiapentalene)(2-methyl-4-(4'-trimethylsilylphenylindenyl)zirconium dichloride,
dimethylsilanediyl(2-methyl-4-oxapentalene)(2-methyl-4-(4'-trimethylsilylphenylindenyl)zirconium dichloride,
dimethylsilanediyl(2-methyl-5-oxapentalene)(2-methyl-4-(4'-trimethylsilylphenylindenyl)zirconium dichloride,
dimethylsilanediyl(2-methyl-6-oxapentalene)(2-methyl-4-(4'-trimethylsilylphenylindenyl)zirconium dichloride,
dimethylsilanediyl(2,5-diethyl-4-oxapentalene)(2-methyl-4-(4'-trimethylsilylphenylindenyl)zirconium dichloride,
dimethylsilanediyl(2,5-dimethyl-6-oxapentalene)(2-methyl-4-(4'-trimethylsilylphenylindenyl)zirconium dichloride,
dimethylsilanediyl(2-methyl-4-azapentalene)(2-methyl-4-(4'-adamantylphenylindenyl)zirconium dichloride,
dimethylsilanediyl(2-methyl-5-azapentalene)(2-methyl-4-(4'-adamantylphenylindenyl)zirconium dichloride,
dimethylsilanediyl(2-methyl-6-azapentalene)(2-methyl-4-(4'-adamantylphenylindenyl)zirconium dichloride,
dimethylsilanediyl(2-methyl-N-phenyl-4-azapentalene)(2-methyl-4-(4'-adamantylphenylindenyl)zirconium dichloride,
dimethylsilanediyl(2-methyl-N-phenyl-5-azapentalene)(2-methyl-4-(4'-adamantylphenylindenyl)zirconium dichloride,
dimethylsilanediyl(2-methyl-N-phenyl-6-azapentalene)(2-methyl-4-(4'-adamantylphenylindenyl)zirconium dichloride,
dimethylsilanediyl(2,5-dimethyl-4-azapentalene)(2-methyl-4-(4'-adamantylphenylindenyl)zirconium dichloride,
dimethylsilanediyl(2,5-dimethyl-6-azapentalene)(2-methyl-4-(4'-adamantylphenylindenyl)zirconium dichloride,
dimethylsilanediyl(2,5-dimethyl-4-azapentalene)(2-methyl-4-(4'-adamantylphenylindenyl)zirconium dichloride,
dimethylsilanediyl(2,5-dimethyl-N-phenyl-4-azapentalene)(2-methyl-4-(4'-adamantylphenylindenyl)zirconium dichloride,
dimethylsilanediyl(2,5-dimethyl-N-phenyl-6-azapentalene)(2-methyl-4-(4'-adamantylphenylindenyl)zirconium dichloride,
dimethylsilanediyl(2-methyl-4-thiapentalene)(2-methyl-4-(4'-adamantylphenylindenyl)zirconium dichloride,
dimethylsilanediyl(2-methyl-5-thiapentalene)(2-methyl-4-(4'-adamantylphenylindenyl)zirconium dichloride,
dimethylsilanediyl(2-methyl-6-thiapentalene)(2-methyl-4-(4'-adamantylphenylindenyl)zirconium dichloride,
dimethylsilanediyl(2,5-dimethyl-4-thiapentalene)(2-methyl-4-(4'-adamantylphenylindenyl)zirconium dichloride,
dimethylsilanediyl(2,5-dimethyl-6-thiapentalene)(2-methyl-4-(4'-adamantylphenylindenyl)zirconium dichloride, dimethylsilanediyl(2-methyl-4-oxapentalene)(2-methyl-4-(4'-adamantylphenylindenyl)zirconium dichloride,
dimethylsilanediyl(2-methyl-5-oxapentalene)(2-methyl-4-(4'-adamantylphenylindenyl)zirconium dichloride,
dimethylsilanediyl(2-methyl-6-oxapentalene)(2-methyl-4-(4'-adamantylphenylindenyl)zirconium dichloride,
dimethylsilanediyl(2,5-dimethyl-4-oxapentalene)(2-methyl-4-(4'-adamantylphenylindenyl)zirconium dichloride,
dimethylsilanediyl(2,5-dimethyl-6-oxapentalene)(2-methyl-4-(4'-adamantylphenylindenyl)zirconium dichloride,
dimethylsilanediyl(2-methyl-4-azapentalene)(2-methyl-4-(4'-tris-(trifluoroethyl)methylphenylindenyl) zirconium dichloride,
dimethylsilanediyl(2-methyl-5-azapentalene(2-methyl-4-(4''-tris(trifluoromethyl)methylphenylindenyl) zirconium dichloride,
dimethylsilanediyl(2-methyl-6-azapentalene)(2-methyl-4-(4'-tris(trifluoromethyl)methylphenylindenyl)zirconium dichloride,
dimethylsilanediyl(2-methyl-N-phenyl-4-azapentalene)(2-methyl-4-(4'-tris(trifluoromethyl)ethylphenylindenyl)zirconium dichloride,
dimethylsilanediyl(2-methyl-N-phenyl-5-azapentalene)(2-methyl-4-(4'-tris(trifluoroethyl)methylphenylindenyl)zirconium dichloride,
dimethylsilanediyl(2-methyl-N-phenyl-6-azapentalene)(2-methyl-4-(4'-tris(trifluoromethyl)methylphenylindenyl)zirconium dichloride,
dimethylsilanediyl(2,5-dimethyl-4-azapentalene)(2-methyl-4-(4'-tris(trifluoromethyl)methylphenylindenyl)zirconium dichloride,
dimethylsilanediyl(2,5-dimethyl-6-azapentalene)(2-methyl-4-(4'-tris(trifluoromethyl)methylphenylindenyl)zirconium dichloride,
dimethylsilanediyl(2,5-dimethyl-N-phenyl-4-azapentalene)(2-methyl-4-(4'-tris(trifluoromethyl)methylphenylindenyl)zirconium dichloride,
dimethylsilanediyl(2,5-dimethyl-N-phenyl-6-azapentalene)(2-methyl-4-(4'-tris(trifluoromethyl)methylphenylindenyl)zirconium dichloride,
dimethylsilanediyl(2-methyl-4-thiapentalene)(2-methyl-4-(4'-tris(trifluoromethyl)methylphenylindenyl)zirconium dichloride,
dimethylsilanediyl(2-methyl-5-thiapentalene)(2-methyl-4-(4'-tris(trifluoromethyl)methylphenylindenyl)zirconium dichloride,
dimethylsilanediyl(2-methyl-6-thiapentalene)(2-methyl-4-(4'-tris(trifluoromethyl)methylphenylindenyl)zirconium dichloride,
dimethylsilanediyl(2,5-dimethyl-4-thiapentalene)(2-methyl-4-(4'-tris(trifluoromethyl)methylphenylindenyl)zirconium dichloride,
dimethylsilanediyl(2,5-dimethyl-6-thiapentalene)(2-methyl-4-(4'-tris(trifluoromethyl)methylphenylindenyl)zirconium dichloride,
dimethylsilanediyl(2-methyl-4-oxapentalene)(2-methyl-4-(4'-tris(trifluoromethyl)methylphenylindenyl) zirconium dichloride,
dimethylsilanediyl(2-methyl-5-oxapentalene)(2-methyl-4-(4'-tris-(trifluoromethyl)methylphenylindenyl) zirconium dichloride,
dimethylsilanediyl(2-methyl-6-oxapentalene)(2-methyl-4-(4'-tris-(trifluoromethyl)methylphenylindenyl)zirconium dichloride,
dimethylsilanediyl(2,5-dimethyl-4-oxapentalene)(2-methyl-4-(4'-tris(trifluoromethyl)methylphenylindenyl) zirconium dichloride,
dimethylsilanediyl(2,5-dimethyl-6-oxapentalene)(2-methyl-4-(4'-tris(trifluoromethyl)methylphenylindenyl) zirconium dichloride,
dimethylsilanediyl(2-methyl-4-azapentalene)(2-ethyl-4-(4'-tert-butylphenylindenyl)zirconium dichloride,
dimethylsilanediyl(2-methyl-5,6-dihydro-4-azapentalene)(2-ethyl-4-(4'-tert-butylphenylindenyl)zirconium dichloride,
dimethylsilanediyl(2-methyl-4-azapentalene)(2-ethyl-4-(4'-tert-butylphenyltetrahydroindenyl)zirconium dichloride,
dimethylsilanediyl(2-methyl-5-azapentalene)(2-n-butyl-4-(4'-tert-butylphenylindenyl)zirconium dichloride,
ethylidene(2-methyl-6-azapentalene)(2-methyl-4-(4'-tert-butylphenylindenyl)zirconium dichloride,
dimethylsilanediyl(2-methyl-N-dimethylsilyl-4-azapentalene)(2-methyl-4-(4'-tert-butylphenylindenyl)zirconium dichloride,
dimethylsilanediyl(2-methyl-N-tolyl-5-azapentalene)(2-n-propyl-4-(4'-tert-butylphenylindenyl)zirconium dichloride,
dimethylgermyldiyl(2-methyl-N-phenyl-6-azapentalene)(2-methyl-4-(4'-tert-butylphenylindenyl)zirconium dichloride,
methylethylidene(2,5-dimethyl-4-azapentalene)(2-methyl-4-(4'-tert-butylphenylindenyl)zirconium dichloride,
dimethylsilanediyl(2,5-diisopropyl-6-azapentalene)(2-methyl-4-(4'-tert-butylphenylindenyl)zirconium dichloride,
dimethylsilanediyl(2,5-dimethyl-N-phenyl-4-azapentalene)(2,6-dimethyl-4-(4'-tert-butylphenylindenyl)zirconium dichloride,
dimethylsilanediyl(2,5-dimethyl-N-phenyl-6-azapentalene)(2-methyl-4-(6'-tert-butylnaphthylindenyl)zirconium dichloride,
dimethylsilanediyl(2,5-dimethyl-N-phenyl-6-azapentalene)(2-methyl-4-(6'-tert-butylanthracenylindenyl)zirconium dichloride,
dimethylsilanediyl(2-methyl-4-phosphapentalane)(2-methyl-4-(4'-tert-butylphenylindenyl)zirconium dichloride,
diphenylsilanediyl(2-methyl-5-thiapentalene)(2-methyl-4-(4'-tert-butylphenylindenyl)zirconium dichloride,
methylphenylsilanediyl(2-methyl-6-thiapentalene)(2-methyl-4-(4'-tert-butylphenylindenyl)zirconium dichloride,
methylidene(2,5-dimethyl-4-thiapentalene)(2-methyl-4-(4'-tert-butylphenylindenyl)zirconium dichloride,
dimethylmethylidene(2,5-dimethyl-6-thiapentalene)(2-methyl-4-(4'-tert-butylphenylindenyl)zirconium dichloride,
diphenylsilanediyl(2,5-dimethyl-4-oxapentalene)(2-methyl-4-(4'-tert-butylphenylindenyl)zirconium dichloride,
diphenylsilanediyl(2,5-dimethyl-6-oxapentalene)(2-methyl-4-(4'-tert-butylphenylindenyl)zirconium dichloride,
dimethylsilanediyl(2-methyl-4-azapentalene)(2-methylindenyl)-zirconium dichloride,
dimethylsilanediyl(2-methyl-5-azapentalene)(2-methylindenyl)-zirconium dichloride,
dimethylsilanediyl(2-methyl-6-azapentalene)(2-methylindenyl)-zirconium dichloride,
dimethylsilanediyl(2-methyl-N-phenyl-4-azapentalene)(2-methylindenyl)zirconium dichloride,
dimethylsilanediyl(2-methyl-N-phenyl-5-azapentalene)(2-methylindenyl)zirconium dichloride,
dimethylsilanediyl(2-methyl-N-phenyl-6-azapentalene)(2-methylindenyl)zirconium dichloride,
dimethylsilanediyl(2,5-dimethyl-4-azapentalene)(2-methylindenyl)-zirconium dichloride, dimethylsilanediyl(2,5-dimethyl-6-azapentalene)(2-methylindenyl)-zirconium dichloride,
dimethylsilanediyl(2,5-dimethyl-N-phenyl-4-azapentalene)(2-methylindenyl)zirconium dichloride,
dimethylsilanediyl(2,5-dimethyl-N-phenyl-6-azapentalene)(2-methylindenyl)zirconium dichloride,
dimethylsilanediyl(2-methyl-4-thiapentalene)(2-methylindenyl)-zirconium dichloride,
dimethylsilanediyl(2-methyl-5-thiapentalene)(2-methylindenyl)-zirconium dichloride,
dimethylsilanediyl(2-methyl-6-thiapentalene)(2-methylindenyl)-zirconium dichloride,
dimethylsilanediyl(2,5-dimethyl-4-thiapentalene)(2-methylindenyl)zirconium dichloride,
dimethylsilanediyl(2,5-dimethyl-6-thiapentalene)(2-methylindenyl)zirconium dichloride,
dimethylsilanediyl(2-methyl-4-oxapentalene)(2-methylindenyl)-zirconium dichloride,
dimethylsilanediyl(2-methyl-5-oxapentalene)(2-methylindenyl)-zirconium dichloride,
dimethylsilanediyl(2-methyl-6-oxapentalene)(2-methylindenyl)-zirconium dichloride,
dimethylsilanediyl(2,5-dimethyl-4-oxapentalene)(2-methylindenyl)-zirconium dichloride,
dimethylsilanediyl(2,5-dimethyl-6-azapentalene)(2-methylindenyl)-zirconium dichloride,
dimethylsilanediyl(2-methyl-4-azapentalene)(indenyl)zirconium dichloride,
dimethylsilanediyl(2-methyl-5-azapentalene)(indenyl)zirconium dichloride,
dimethylsilanediyl(2-methyl-6-azapentalene)(indenyl)zirconium dichloride,
dimethylsilanediyl(2-methyl-N-phenyl-4-azapentalene)(indenyl)-zirconium dichloride,
dimethylsilanediyl(2-methyl-N-phenyl-5-azapentalene)(indenyl)-zirconium dichloride,
dimethylsilanediyl(2-methyl-N-phenyl-6-azapentalene)(indenyl)-zirconium dichloride,
dimethylsilanediyl(2,5-methyl-4-azapentalene)(indenyl)-zirconium dichloride,
dimethylsilanediyl(2,5-dimethyl-6-azapentalene)(indenyl)-zirconium dichloride,
dimethylsilanediyl(2,5-dimethyl-N-phenyl-4-azapentalene)-(indenyl)zirconium dichloride,
dimethylsilanediyl(2,5-dimethyl-N-phenyl-6-azapentalene)-(indenyl)zirconium dichloride,
dimethylsilanediyl(2-dimethyl-4-thiapentalene)(indenyl)zirconium dichloride,
dimethylsilanediyl(2-methyl-5-thiapentalene)(indenyl)zirconium dichloride,
dimethylsilanediyl(2-methyl-6-thiapentalene)(indenyl)zirconium dichloride, dimethylsilanediyl(2,5-dimethyl-4-thiapentalene)(indenyl)-zirconium dichloride,
dimethylsilanediyl(2,5-dimethyl-6-thiapentalene)(indenyl)-zirconium dichloride,
dimethylsilanediyl(2-methyl-4-oxapentalene)(indenyl)zirconium dichloride,
dimethylsilanediyl(2-methyl-5-oxapentalene)(indenyl)zirconium dichloride,
dimethylsilanediyl(2-methyl-6-oxapentalene)(indenyl)zirconium dichloride,
dimethylsilanediyl(2,5-dimethyl-4-oxapentalene)(indenyl)-zirconium dichloride,
dimethylsilanediyl(2,5-dimethyl-6-oxapentalene)(indenyl)-zirconium dichloride,
dimethylsilanediyl(2-methyl-4-azapentalene)(2-methyl-4-phenylindenyl)zirconium dichloride,
dimethylsilanediyl(2-methyl-5-azapentalene)(2-methyl-4-phenylindenyl)zirconium dichloride,
dimethylsilanediyl(2-methyl-6-azapentalene)(2-methyl-4-phenylindenyl)zirconium dichloride,
dimethylsilanediyl(2-methyl-N-phenyl-4-azapentalene)(2-methyl-4-phenylindenyl)zirconium dichloride,
dimethylsilanediyl(2-methyl-N-phenyl-5-azapentalene)(2-methyl-4-phenylindenyl)zirconium dichloride,
dimethylsilanediyl(2-methyl-N-phenyl-6-azapentalene)(2-methyl-4-phenylindenyl)zirconium dichloride,
dimethylsilanediyl(2,5-dimethyl-4-azapentalene)(2-methyl-4-phenylindenyl)zirconium dichloride,
dimethylsilanediyl(2,5-dimethyl-6-azapentalene)(2-methyl-4-phenylindenyl)zirconium dichloride,
dimethylsilanediyl(2,5-dimethyl-N-phenyl-4-azapentalene)(2-methyl-4-phenylindenyl)zirconium dichloride,
dimethylsilanediyl(2,5-dimethyl-N-phenyl-6-azapentalene)(2-methyl-4-phenylindenyl)zirconium dichloride,
dimethylsilanediyl(2-methyl-4-thiapentalene)(2-methyl-4-phenylindenyl)zirconium dichloride,
dimethylsilanediyl(2-methyl-5-thiapentalene)(2-methyl-4-phenylindenyl)zirconium dichloride,
dimethylsilanediyl(2-methyl-6-thiapentalene)(2-methyl-4-phenylindenyl)zirconium dichloride,
dimethylsilanediyl(2,5-dimethyl-4-thiapentalene)(2-methyl-4-phenylindenyl)zirconium dichloride,
dimethylsilanediyl(2,5-dimethyl-6-thiapentalene)(2-methyl-4-phenylindenyl)zirconium dichloride,
dimethylsilanediyl(2-methyl-4-oxapentalene)(2-methyl-4-phenylindenyl)zirconium dichloride,
dimethylsilanediyl(2-methyl-5-oxapentalene)(2-methyl-4-phenylindenyl)zirconium dichloride,
dimethylsilanediyl(2-methyl-6-oxapentalene)(2-methyl-4-phenylindenyl)zirconium dichloride,
dimethylsilanediyl(2,5-dimethyl-4-oxapentalene)(2-methyl-4-phenylindenyl)zirconium dichloride,
dimethylsilanediyl(2,5-dimethyl-6-oxapentalene)(2-methyl-4-phenylindenyl)zirconium dichloride,
dimethylsilanediyl(2-methyl-4-azapentalene)(2-methyl-4,5-benzoindenyl)zirconium dichloride,
dimethylsilanediyl(2-methyl-5-azapentalene)(2-methyl-4,5-benzoindenyl)zirconium dichloride,
dimethylsilanediyl(2-methyl-6-azapentalene)(2-methyl-4,5-benzoindenyl)zirconium dichloride,
dimethylsilanediyl(2-methyl-N-phenyl-4-azapentalene)(2-methyl-4,5-benzoindenyl)zirconium dichloride,
dimethylsilanediyl(2-methyl-N-phenyl-5-azapentalene)(2-methyl-4,5-benzoindenyl)zirconium dichloride,
dimethylsilanediyl(2-methyl-N-phenyl-6-azapentalene)(2-methyl-4,5-benzoindenyl)zirconium dichloride,
dimethylsilanediyl(2,5-dimethyl-4-azapentalene)(2-methyl-4,5-benzoindenyl)zirconium dichloride,
dimethylsilanediyl(2,5-dimethyl-6-azapentalene)(2-methyl-4,5-benzoindenyl)zirconium dichloride,
dimethylsilanediyl(2,5-dimethyl-N-phenyl-4-azapentalene)(2-methyl-4,5-benzoindenyl)zirconium dichloride,
dimethylsilanediyl(2,5-dimethyl-N-phenyl-6-azapentalene)(2-methyl-4,5-benzoindenyl)zirconium dichloride,
dimethylsilanediyl(2-methyl-4-thiapentalene)(2-methyl-4,5-benzoindenyl)zirconium dichloride,
dimethylsilanediyl(2-methyl-5-thiapentalene)(2-methyl-4,5-benzoindenyl)zirconium dichloride,
dimethylsilanediyl(2-methyl-6-thiapentalene(2-methyl-4,5-benzoindenyl)zirconium dichloride,
dimethylsilanediyl(2,5-dimethyl-4-thiapentalene)(2-methyl-4,5-benzoindenyl)zirconium dichloride,
dimethylsilanediyl(2,5-dimethyl-6-thiapentalene)(2-methyl-4,5-benzoindenyl)zirconium dichloride,
dimethylsilanediyl(2-methyl-4-oxapentalene)(2-methyl-4,5-benzoindenyl)zirconium dichloride,
dimethylsilanediyl(2-methyl-5-oxapentalene)(2-methyl-4,5-benzoindenyl)zirconium dichloride, dimethylsilanediyl(2-methyl-6-oxapentalene)(2-methyl-4,5-benzoindenyl)zirconium dichloride,
dimethylsilanediyl(2,5-dimethyl-4-oxapentalene)(2-methyl-4,5-benzoindenyl)zirconium dichloride,
dimethylsilanediyl(2,5-dimethyl-6-oxapentalene)(2-methyl-4,5-benzoindenyl)zirconium dichloride,
dimethylsilanediylbis(2-methyl-4-azapentalene)zirconium dichloride,
dimethylsilanediylbis(2-methyl-5-azapentalene)zirconium dichloride,
dimethylsilanediylbis(2-methyl-6-azapentalene)zirconium dichloride,
dimethylsilanediylbis(2-methyl-N-phenyl-4-azapentalene)zirconium dichloride,
dimethylsilanediylbis(2-methyl-N-phenyl-5-azapentalene)zirconium dichloride,
dimethylsilanediylbis(2-methyl-N-phenyl-6-azapentalene)zirconium dichloride,
dimethylsilanediylbis(2,5-dimethyl-4-azapentalene)zirconium dichloride,
dimethylsilanediylbis(2,5-dimethyl-6-azapentalene)zirconium dichloride,
dimethylsilanediylbis(2,5-dimethyl-N-phenyl-4-azapentalene)-zirconium dichloride,
dimethylsilanediylbis(2,5-dimethyl-N-phenyl-6-azapentalene)-zirconium dichloride,
dimethylsilanediylbis(2-methyl-4-thiapentalene)zirconium dichloride,
dimethylsilanediylbis(2-methyl-5-thiapentalene)zirconium dichloride,
dimethylsilanediylbis(2-methyl-6-thiapentalene)zirconium dichloride,
dimethylsilanediylbis(2,5-dimethyl-4-thiapentalene)zirconium dichloride,
dimethylsilanediylbis(2,5-dimethyl-6-thiapentalene)zirconium dichloride,
dimethylsilanediylbis(2-methyl-4-oxapentalene)zirconium dichloride,
dimethylsilanediylbis(2-methyl-5-oxapentalene)zirconium dichloride,
dimethylsilanediylbis(2-methyl-6-oxapentalene)zirconium dichloride,
dimethylsilanediylbis(2,5-dimethyl-4-oxapentalene)zirconium dichloride,
dimethylsilanediylbis(2,5-dimethyl-6-oxapentalene)zirconium dichloride.

Further examples of metallocenes which can be used according to the present invention are the metallocenes in which the zirconium, fragment "-zirconium dichloride" is replaced by
zirconium monochloride mono(2,4-di-tert-butylphenoxide),
zirconium monochloride mono(2,6-di-tert-butylphenoxide),
zirconium monochloride mono(3,5-di-tert-butylphenoxide),
zirconium monochloride mono(2,6-di-sec-butylphenoxide),
zirconium monochloride mono(2,4-dimethylphenoxide),
zirconium monochloride mono(2,3-dimethylphenoxide),
zirconium monochloride mono(2,5-dimethylphenoxide),
zirconium monochloride mono(2,6-dimethylphenoxide),
zirconium monochloride mono(3,4-dimethylphenoxide),
zirconium monochloride mono(3,5-dimethylphenoxide),
zirconium monochloride monophenoxide,
zirconium monochloride mono(2-methylphenoxide),
zirconium monochloride mono(3-methylphenoxide),
zirconium monochloride mono(4-methylphenoxide),
zirconium monochloride mono(2-ethylphenoxide),
zirconium monochloride mono (3-ethylphenoxide),
zirconium monochloride mono(4-ethylphenoxide),
zirconium monochloride mono(2-sec-butylphenoxide),
zirconium monochloride mono(2-tert-butylphenoxide),
zirconium monochloride mono(3-tert-butylphenoxide),
zirconium monochloride mono(4-sec-butylphenoxide),
zirconium monochloride mono(4-tert-butylphenoxide),
zirconium monochloride mono(2-isopropyl-5-methylphenoxide),
zirconium monochloride mono(4-isopropyl-3-methylphenoxide),
zirconium monochloride mono(5-isopropyl-2-methylphenoxide),
zirconium monochloride mono(5-isopropyl-3-methylphenoxide),
zirconium monochloride mono(2,4-bis-(2-methyl-2-butyl) phenoxide),
zirconium monochloride mono(2,6-di-tert-butyl-4-methylphenoxide),
zirconium monochloride mono(4-nonylphenoxide),
zirconium monochloride mono(1-naphthoxide),
zirconium monochloride mono(2-naphthoxide),
zirconium monochloride mono(2-phenylphenoxide),
zirconium monochloride mono(tert-butoxide),
zirconium monochloride mono(N-methylanilide),
zirconium monochloride mono(2-tert-butylanilide),
zirconium monochloride mono(tert-butylamide),
zirconium monochloride mono(di-isopropylamide),
monomethyl zirconium monochloride,
monobenzyl zirconium monochloride,
mononeopentyl zirconium monochloride.

Preference is also given to the corresponding dimethyl zirconium compounds and the corresponding η$^4$-butadienezirconium, compounds.

The catalyst systems of the present invention preferably comprise at least one alkyl compound of an element of main group III or IV of the Periodic Table of the Elements, which preferably corresponds to the formula (III), usually an organometallic compound which can be reacted in any stoichiometric ratio with compounds of the formula (I) or (II)

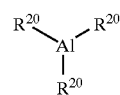

III

The radicals $R^{20}$ in formula (III) may be identical or different and can be a halogen atom, a hydrogen atom or a $C_1$–$C_{40}$ group, preferably $C_1$–$C_{20}$-alkyl, $C_1$–$C_{20}$-haloalkyl, $C_6$–$C_{20}$-aryl, $C_6$–$C_{20}$-haloaryl, $C_7$–$C_{40}$-arylalkyl, $C_7$–$C_{40}$-haloarylalkyl, $C_7$–$C_{40}$-alkylaryl or $C_7$–$C_{40}$-haloalkylaryl. $R^{20}$ are preferably $C_1$–$C_6$-alkyl groups, particularly preferably $C_1$–$C_4$-alkyl groups.

The preparation of the catalyst systems of the present invention will be described for boron as representative for elements of group III of the Periodic Table of the Elements. The catalyst system of the present invention is prepared using a molar ratio of boron:$M^2$ in the compounds of the formula (I) and the formula (II) of from 0.01 to 10,000. Preference is given to using a molar ratio of from 0.1 to 1000, very particularly preferably from 1 to 100. For this purpose, a compound of the formula (III) can be additionally added in a molar ratio of Al:$M^2$ of from 0.01 to 10,000. Preference is giver to using a molar ratio of from 0.1 to 1000, very particularly preferably from 1 to 100.

The compounds can be brought into contact with one another in a variety of ways. In one possible procedure, an organometallic transition metal compound of the formula (II) is dissolved or suspended in an aliphatic or aromatic solvent, e.g. toluene, heptane, tetrahydrofuran, methyl tert-butyl ether, dimethoxyethane, diisopropyl ether, di-n-butyl ether or diethyl ether.

Subsequently, preferably a compound of the formula (III) is added in dissolved or suspended form. The reaction time is from 1 minute to 24 hours, preferably from 5 minutes to 120 minutes. The reaction temperature is generally in the range from −10° C. to +200° C., preferably from 0° C. to 50° C. After this, a compound of the formula (I), in particular an organoboron compound of the formula (I), is added either as such or in dissolved or suspended form. The reaction tire is generally from 1 minute to 24 hours, preferably from 5 minutes to 120 minutes. The reaction temperature is in the range from −10° C. to +200° C., preferably from 0° C. to 50° C. The individual components can also be introduced successively in any order into the polymerization vessel.

If desired, the catalyst system of the present invention can also be used in supported form. For this purpose, the catalyst system of the present invention can be reacted with a support component: the catalyst system of the present invention preferably comprises at least one support component (C) which can be any organic or inorganic, inert solid. In particular, the support component (C) can be a porous support such as talc, inorganic oxides and finely divided polymer powders (e.g. polyolefins).

Suitable inorganic oxides may be found among those of elements of groups 2, 3, 4, 5, 13, 14, 15 and 16 of the Periodic Table of the Elements. Examples of oxides preferred as support include silicon dioxide, aluminum oxide and mixed oxides of the two elements and corresponding oxide mixtures. Other inorganic oxides which can be used alone or in combination with the abovementioned preferred oxidic supports are, for example, MgO, $ZrO_2$, $TiO_2$ or $B_2O_3$.

The support materials used preferably have a specific surface area in the range from 10 to 1000 $m^2/g$, a pore volume in the range from 0.1 to 5 ml/g and a mean particle size of from 1 to 500 μm. Preference is given to supports having a specific surface area in the range from 50 to 500 μm, a pore volume in the range from 0.5 to 3.5 ml/g and a mean particle size in the range from 5 to 350 μm. Particular preference is given to supports having a specific surface area in the range from 200 to 400 $m^2/g$, a pore volume in the range from 0.8 to 3.0 ml/g and a mean particle size of from 10 to 200 μm.

If the support material used naturally has a low moisture content or residual solvent content, dehydration or drying before use can be omitted. If this is not the case, for example when using silica gel as support material, dehydration or drying is advisable Thermal dehydration or drying of the support material can be carried out under reduced pressure with simultaneous blanketing with inert gas (e.g. nitrogen). The drying temperature is in the range from 100 to 1000° C., preferably from 200 to 800° C. The parameter pressure is not critical in this case. The drying time can be from 1 to 24 hours. Shorter or longer drying times are possible, provided that equilibrium with the hydroxyl groups on the support surface can be established under the conditions chosen, which normally takes from 4 to 8 hours.

The support material can also be dehydrated or dried by chemical means, by reacting the adsorbed water and the hydroxyl groups on the surface with suitable passivating agents. The reaction with the passivating reagent can convert all or some of the hydroxyl groups into a form which leads to no adverse interaction with the catalytically active centers. Suitable passivating agents are, for example, silicon halides and silanes, e.g. silicon tetrachloride, chlorotrimethylsilane or dimethylaminotrichlorosilane, or organometallic compounds of aluminum, boron and magnesium, e.g. trimethylaluminum, triethylaluminum, triisobutylaluminum, triethylborane or dibutylmagnesium. The chemical dehydration or passivation of the support material is carried out, for example, by reacting a suspension of the support material in a suitable solvent in the absence of air and moisture with the passivating reagent in pure form or as a solution in a suitable solvent. Suitable solvents are, for example, aliphatic or aromatic hydrocarbons such as pentane, hexane, heptane, toluene or xylene. Passivation is generally carried out a, from 25° C. to 120° C., preferably from 50° C. to 70° C. The reaction time is usually from 30 minutes to 20 hours, preferably from 1 to 5 hours. After chemical dehydration is complete, the support material can be isolated by filtration under inert conditions, washed one or more times with suitable inert solvents, like those described above, and subsequently dried in a stream of inert gas or under reduced pressure.

Organic support materials such as finely divided polyolefin powders (e.g. polyethylene, polypropylene or polystyrene) are likewise suitable for use according to the present invention. These should preferably likewise be freed of adhering moisture, solvent residues or other impurities by appropriate purification and drying operations before use.

To apply the catalyst system of the present invention to a support, the catalyst mixture prepared as described above is generally mixed with a dehydrated or passivated support material, the solvent is removed and the resulting supported metallocene catalyst system is dried to ensure that all or most of the solvent is removed from the pores of the support material. The supported catalyst is obtained as a free-flowing powder.

Preference is given to polymerizing olefins of the formula $R_m$—CH=CH—$R_n$, where $R_m$ and $R_n$ are identical or different and are each a hydrogen atom or an organic radical having from 1 to 20 carbon atoms, in particular from 1 to 10 carbon atoms, or $R_m$ and $R_n$ together with the atoms connecting them may form one or more rings.

Examples of such olefins are 1-olefins having 2–40, preferably from 2 to 10, carbon atoms, e.g. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene or ethylnorbornadiene and cyclic olefins such as norbornene, tetracyclododecene or methylnorbornene. In the process of the present invention, preference is given to homopolymerizing propene or ethene or copolymerizing propene with ethene and/or wit) one or more 1-olefins having from 4 to 20 carbon atoms, e.g. hexene, and/or one or more dienes having from 4 to 20 carbon atoms, e.g. 1,4-butadiene, norbornadiene, ethylidenenorbornene or ethylnorbornadiene. Examples of such copolymers are ethene-propene copolymers and ethene-propene-1,4-hexadiene terpolymers.

The polymerization is generally carried out at from −60° C. to 300° C., preferably from 50° C. to 200° C., very particularly preferably from 50° C. to 80° C. The pressure is generally from 0.5 to 2000 bar, preferably from 5 to 64 bar.

The polymerization can be carried out in solution, in bulk, in suspension or in the gas phase, continuously or batchwise, in one or more stages.

The catalyst system prepared according to the present invention can be used as sole catalyst component for the polymerization of olefins having from 2 to 20 carbon atoms, or preferably in combination with at least one alkyl compound of an element of main groups I to III of the Periodic Table, e.g. an aluminum, magnesium or lithium alkyl or an aluminoxane. The alkyl compound is added to the monomer or suspension medium and serves to free the monomer of substances which can adversely affect the catalyst activity. The amount of alkyl compound added depends on the quality of the monomers used.

If necessary, hydrogen is added as molar mass regulator and/or to increase the activity.

The supported catalyst system can be used directly for the polymerization. However, it is also possible to remove the solvent and resuspend the catalyst system for use in the polymerization. The advantage of this activation method is that it makes it possible to allow the polymerization-active catalyst system to be formed only in the reactor. This prevents partial decomposition from occurring on introduction of the air-sensitive catalyst.

Furthermore, an additive such as an antistatic can be used in the process of the present invention, e.g. for improving the particle morphology of the polymer.

It is generally possible to use all antistatics which are suitable for polymerization. Examples are salt mixtures of calcium salts of Medialan acid and chromium salts of N-stearylantranilic acid, as described in DE-A-3,543,360. Further suitable antistatics are, for example, $C_{12}$–$C_{22}$-fatty acid soaps of alkali or alkaline earth metals, salts of sulfonic esters, esters of polyethylene glycols with fatty acids, polyoxyethylene alkyl ethers, etc. A review of antistatics is given in EP-A-0 107 127.

It is also possible to use a mixture of a metal salt of Medialan acid, a metal salt or anthranilic acid and a polyamine, as described in EP-A-0 636 636, as antistatic.

Commercially available products such as Stadis® 450 from DuPont, namely a mixture of toluene, isopropanol, dodecylbenzenesulfonic acid, a polyamine, a copolymer of 1-decene and $SO_2$ plus 1-decene or ASA®-3 from Shell and ARU5R® 163 from ICI can likewise be used.

The antistatic is preferably used as a solution. In the preferred case of Stadis® 450, preference is given to using from 1 to 50% by weight of this solution, preferably from 5 to 25% by weight, based on the mass of the supported catalyst used (support together with covalently bound metallocenium-forming compound and one or more metallocene compounds, e.g. of the formula (II).

However, the required amount of antistatic can fluctuate within a wide range, depending on the type of antistatic used.

The polymers prepared using the catalyst system of the present invention display a uniform particle morphology and contain no fines. In the polymerization using the catalyst system of the present invention, no deposits or cake material are formed.

The novel compounds of the formula (I) and catalyst systems according to the present invention containing these compounds have the advantage that the starting materials are not carcinogenic, mutagenic or extremely toxic. In addition, the good solubility of the compounds of the formula (I) leads to virtually completely reacted catalyst systems. This results in high cost savings and thus advantageous commercial utilization.

The polymers prepared by the process of the present inventor are particularly suitable for producing hard and stiff shaped bodies having a good tensile strength, e.g. fibers, filaments, injection-molded parts, films, sheets or large hollow bodies (e.g. pipes).

The above-described preparation of a possible catalyst system is preferably carried out according to the following sequence.

In a first step A, an inorganic support material as described under C is reacted with a metal compound of the formula (III). The metal compound of the formula (III) is preferably added as a solution to a suspension of the support. Solvents or suspension media used are those described under B. The amount of metal compounds of the formula (III) can be varied within wide limits, and the minimum amount depends on the number of hydroxy groups on the support. Temperature, reaction times and pressures are not critical per se; preference is given to the temperatures and reaction times described under step B. After pretreatment of the support, it has been found to be useful to remove the excess metal compound of the formula (III) by washing, for example with hydrocarbons such as pentane, hexane, ethylbenzene or heptane, and to dry the support.

This material is then, in a further step B, mixed with a metal complex of the formula (II) and a compound capable of forming metallocenium ions. It is also possible to use mixtures of various metallocene complexes.

Suitable compounds capable of forming metallocenium ions are, in particular, the novel compounds of the formula (I). The conditions for the reaction of the metallocene complex with the metallocenium-forming compound of the formula (I) are not critical per se; the reaction is preferably carried out in solution, with suitable solvents being, in particular, hydrocarbons, preferably aromatic hydrocarbons such as toluene. An amount so from 0.1 to 10% by weight of metallocene complexes, based on the inorganic support material, is particularly useful. The conditions for this reaction are likewise not critical. Temperatures in the range from 20 to 80° C. and reaction times in the range from 0.1 to 20 hours have been found to be particularly useful.

In a further step C, namely the activation step, the material obtained in step B is reacted with a metal compound of the formula (III). This activation can be carried out at any desired point in time, i.e. before, during or after introduction of the material obtained in step B into the reactor. The activation is preferably carried out after the material obtained in step B has been introduced into the reactor.

The novel compounds of the formula (I) have, in particular, a high activity. They can be stored for a long time, are not pyrophoric and are readily soluble.

The following examples illustrate the invention. Owing to the air- and hydrolysis-sensitivity of the compounds, all work was carried out under a protective gas atmosphere (argon) within a glove box or using the Schlenk technique. All solvents (including deuterated solvents) were dried and distilled under argon. The compounds used were either commercially available or were prepared by methods known from the literature.

NMR experiments were carried out on Varian Unity Plus 600, Bruker AC200 P and Bruker ARX300 spectrometers. Chemical shifts are relative to $Me_4Si$ [$\delta^1H(C_6D_5H)$=7.15, $\delta^1H(C_6D_5CD_2H)$=2.03, $\delta^{13}C$ $(C_6D_6)$=128.0, $\delta^{13}C$ $(C_6D_5CD_3)$=20.4], pure $BF_3*OEt_2$ [$\delta^{11}B$=0, $\Theta(^{11}B)$=32.084 MHz], 2% benzamide($^{15}N$), 0.2% $Cr(acac)_3$ in DMSO [$\delta^{15}N$=−279.3 relative to pure $MeNO_2$ $\delta^{15}N$=0, $\Theta(^{15}N)$= 10.133 MHz], $CFCl_3$ ($\delta^{19}F$=0, $\Theta(^{19}F)$=94.077 MHz]. The assignments in the $^1H$— and $^{13}C$-NMR spectra were confirmed by APT (attached proton test), GCOSY (gradient enhanced $^1H$-$^1H$ COSY), 1D-TOCSY ($^1H$ total correlation spectroscopy), 1D-NOEDIF ($^1H$ nuclear overhauser effect difference spectroscopy), GHSQC ($^1H$-$^{13}C$ gradient enhanced heteronuclear single quantum correlation) and GHMBC ($^1H$-$^{13}C$ gradient enhanced heteronuclear multiple bond correlation) experiments. $^{15}N$-NMR-experiments were carried out using a GHMBC pulse sequence ($^nJ(^{15}N, ^1H)$=10 Hz, n=2, 3).

IR spectra were recorded on a Nicolet 5 DXC fourier transform IR spectrometer, U spectra were recorded on a TIDAS (Transputer integrated Diode Array Spectrometer) from J&M by means of a fused quartz emersion probe from HELLMA (path length: 1.00 mm±0.001 mm). Melting points were determined by means of differential scanning calorimetry (DSC 2010 CE from TA Instruments). For elemental analyses use was made of a Foss-Heraeus CHN rapid elemental analyzer.

EXAMPLE 1

Preparation of N-(2-H-pyrrolium)tris(pentafluorophenyl)borate a) Lithium tris(pentafluorophenyl)-N-pyrrolylborate (1)

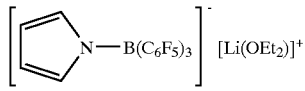

0.531 g (7.27 mmol) of freshly prepared pyrrolyllithium and 3.724 g (7.27 mmol) of tris(pentafluorophenyl)borane were together suspended in 50 ml of diethyl ether. After stirring for three hours at 25° C., the ether was removed under reduced pressure and the residue was taken up in 100 ml of pentane. The resulting suspension was filtered, the residue was washed three times with 20 ml each time of pentane and dried under reduced pressure. The product obtained was a colorless, hydrolysis-sensitive powder containing about 1 equivalent of ether per molecule (4.5 g; about 91% yield). Colorless single crystals crystallized from a pentane/ether solution at 8° C. and an X-ray structure analysis was carried out on these.

Melting point: 137.2° C.

Decomposition point; 204.6° C.

Elemental analysis (%) of $C_{26}H_{14}NBF_{15}LiO$ ($M_r$=659.1): calculated: C 47.38, H 2.14, N 2.13; found: C 47.63, H 2.95, N, 1.90.

MS(m/e)=578 (pyrrolylB($C_6F_5$)$_3$).

UV ($CH_2Cl_2$) ($\lambda$(int))=230.5(0.9158); 260.5(0.5837) nm.

IR-(KBR) v=2985.4, 2964.1, 2905.4, 1646.3, 1628.3, 1517.7, 1463.9, 1445.8, 1386.1, 1372.3, 1280.6, 1262.7, 1204.7, 1094.4, 1068.7, 1019.8, 979.6, 963.7, 867.8, 860.1, 802.4, 792.8, 772.5, 761.4, 750.8, 697.2, 685.2, 678.1, 622.9, 613.5, 575.8 cm$^{-1}$. $^1$H-NMR (599.9 MHz, $C_6D_6$, 298K): δ=6.72 (m, $^1$J(C,H)=184.8 Hz, 2H, H(2,5)), 5.84 (m, $^1$J(C,H)=171.9 Hz, 2H, H(3,4)), 2.80 (q, $^1$J(C,F)=144.3 Hz, 4H, OEt$_2$), 0.68 (t, $^1$J(C,H)=126.3 Hz, 6H, OEt$_2$).

$^1$H-NMR (599.9 MHz, TDF, 298K): δ=6.45 (br., 2H, H(2,5)), 5.7 (m, 2H, H(3,4)) 3.38 (q, $^3$J(H,H)=6.9 Hz, $^1$J(C,H)=139.1 Hz, 4H, OEt$_2$), 1.11 (t, $^3$J(H,H)=6.9 Hz, $^1$J(C,H)=125.6 Hz, 6H., OEt$_2$).

$^{13}$C{1H}-NMR (150.7 MHz, $C_6D_6$, 298K): δ 148.2 (dm, $^1$J(F,C)=234.3 Hz, Ar$^F_{ortho}$), 139.8 (dm, 1J(F,C)=249.8 Hz, Ar$^F_{para}$), 137.6 (dm, $^1$J(F,C)=248.5 Hz, Ar$^F_{meta}$), 121.3 (broad, C$_{ipso}$), 25.0 (C(2,5)), 108.9 (C(3,4)), 65.9, 14.0 (OEt$_2$).

$^{19}$F-NMR (282.4 MHz, $C_6D_6$, 300K): δ=-134.9 (br., 2F, F$_{ortho}$) -157.5 (t, 1F, F$_{para}$), -162.7 (m, 2F, F$_{meta}$).

$^{11}$B{$^1$H}-NMR (64.2 MHz, $C_6D_6$, 300K) δ=-8.2 (v½=50 Hz) $^{11}$B-NMR (192.2 MHz, TDF, 298K) δ=-8.8 (v½=20 Hz). $^7$Li-NMR (77.8.1 MHz, TDF, 300K): δ=-2.6 (v½=2 Hz). $^1$H, $^1$H-GCOSY (599.9/599.9 MHz, $C_6D_6$, 298K): δ$^1$H/δ$^1$H=6.72/5.84 (H(2,5)/H(3,4)), 2.80/0.68 (OEt$_2$/OEt$_2$).

$^1$H, $^{13}$C-GHSQC (599.9/150.7 MHz, $C_6D_6$, 298K): δ$^1$H/δ$^{13}$C=6.72/125.0 (H(2,5)/C(2,5)), 5.84/108.9 (H(3,4)/C(3,4)), 2.80/65.9; 0.68/14.0 (OEt$_2$).

$^1$H, $^{13}$C-GHMBC (599.9/150.7 MHz, $C_6D_6$, 298:9): δ$^1$H/δ$^{13}$C=6.72/108.9 (H(2,5)/C(3,4)), 5.84/125.0 (H(3,4)/C(2,5)), 2.80/14.0; 0.68/65.9 (OEt$_2$).

b) N-(2-H-pyrrolium)tris(pentafluorophenyl)borate (2)

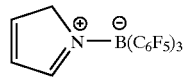

3.0 ml (3.00 mmol) of a 1M hydrogen chloride/ether solution were slowly added dropwise to a solution of 1.50 g (2.56 mmol) of lithium tris(pentafluorophenyl)-N-pyrrolylborate in 60 ml of diethyl ether while stirring vigorously. After 30 minutes, the diethyl ether was removed under reduced pressure and the residue was stirred wish 20 ml of pentane. The resulting suspension was filtered and the residue was extracted three times with cold toluene. The yellowish toluene phases were combined and the solvent was removed under reduced pressure. The product obtained was a light-yellow powder which was purified by fractional crystallization from toluene at -18° C. This gave single crystals on which an X-ray structure analysis was carried out (0.852 g, 1.47 mmol, 57% yield).

Melting point: 178.7° C.

Elemental analysis (%) for $C_{22}H_5NBF_{15}$ ($M_r$=579.1): calculated C 45.63, H 0.87, N 2.42; found: C, 45.50; H, 1.11; N, 2.27. UV ($CH_2Cl_2$)($\lambda$(int))=231.0(0.9482); 254.0 (0.8525) nm.

IR-(KBR) v=2966.3, 2932.8, 1647.0, 1603.1, 1520.6, 1502.5, 1465.2, 1389.6, 1374.0, 1361.4, 1310.7, 1285.1, 1269.8, 1262.7, 1120.0, 1099.6, 1086.4, 1063.7, 1045.0, 972.3, 953.4, 911.3, 906.3, 800.5, 789.3, 773.6, 769.5, 744.6, 739.0, 703.8, 689.6, 682.8, 668.9, 625.7, 614.1, 577.5 cm$^{-1}$.

$^1$H-NMR (599.9 MHz, $C_6D_6$, 298K) δ=7.35 (br., 1H, H(2)), 6.34 (m, 1H, H(4)), 5.45 (m, 1H(3)), 3.53 (br., 2H, H(5)).

$^1$HNMR (599.9 MHz, $C_7D_8$, 213K): δ=6.93 (br., 1H, H(2)), 6.07 (m, 1H, H(4)), 5.20 (m, 1H, H(3)), 3.08 (br., 2H, H(5)).

$^{13}$C-NMR (150.7 MHz, $C_6D_6$, 298K): δ=171.1 (C(2)), 155.5 (C(4)), 148.2 (dm, $^1$J(F,C)=241.4 Hz, Ar$^F_{ortho}$)) 140.6 (dm, $^1$J(F,C)=253.4 Hz, Ar$^F_{para}$), 137.6 (dm, $^1$J(F,C)=249.1 Hz, Ar$^F_{meta}$), 127.2 (C(3)), 118.5 (br., C$_{ipso}$), 65.5 (C(5)).

$^{11}$B-NMR (192.2 MHz, $C_7D_8$, 298K): δ=-7.6 (v½=90 Hz).

$^{19}$F-NMR (563.7 MHz, $C_1D_8$, 298K): δ=-132.3 (m, 2F, F$_{ortho}$), -155.7 (t, 1F$_{para}$), -162.6 (m, 2F, F$_{meta}$).

$^1$H-NOEDIF ((599.9 MHz, $C_6D_6$, 298K): δ(irradiation point)/δ(reply)=7.35 (H(2))/5.45 (H(3)), GCOSY (599.9/599.9 MHz, $C_6D_6$, 298×): δ$^1$H/δ$^1$H=7.35/3.53 (H(2)/H(5)), 6.34/5.45 (H(4)/H(3)).

$^1$H, $^{13}$C-GHSQC (5999/150.7 MHz, $C_6D_6$, 298K): δ1H/δ13C=7.35/171.1 (H(2)/C(2)), 6.34/155.5 (H(4)/C(4)), 5.45/127.2 (F(3)/C(3)), 3.53/65.5 (H(S)/C(5)).

$^1$H, $^{13}$C-GHMBC (599.9/150.7 MHz, $C_6D_6$, 298K): δ1H/δ13C=7.35/155.5, 127.2, 65.5 (H(2)/C(4,3,5)), 6.34/171.1, 127.2, 65.5 (H(4)/C(2,3,5)), 5.45/171.1, 155.5, 65.5 (H(3)/C(2,3,5)), 3.53/171.1, 155.5, 127.2 (H(5)/C(2,3,4)).

$^1$H, $^{15}$N-GHMBC (599.9/60.7 MHz, $C_7D_8$, 213K); δ1H/δ15N=6.93, 6.07, 5.20/-145 (H(2,4,3))/N(1)).

Polymerization Examples and Comparative Examples

Polymerization of Ethene

In a Büchi laboratory autoclave, a solution consisting of 300 ml of toluene and 2–3 ml of tri(isobutyl)aluminum was heated for one hour at the chosen reaction temperature and subsequently saturated with ethene for one hour. The catalyst was freshly generated in 3 ml of toluene by treatment of the organometallic compound with the activator and then this toluene solution was injected directly into the autoclave. The polymerization was stopped by addition of 20 ml of HCl/methanol (1:5; v/v). The resulting polymer was washed in succession with HCl, water, methanol and acetone and was subsequently dried. The amounts of novel activator used in the examples according to the present invention (activator: N-(2-H-pyrrolium) tris(penta-fluorophenyl)-borate)=HBNF) and the comparative examples (activator: MAO, B($C_6F_5$)$_3$, Bu$_3$NHBPH$_4$) and information on the polymers obtained are shown in Table 1.

TABLE 1

| Example/ Comparitive Example | Organometallic compound | Activator | Organometallic compound [mg(μmol)] | Activator) [mg(μmol)] | T [° C.] | P [bar] | Reaction-time [min] | Amount of polymer [g] | Activity [g/mmol Zr-bar-h] | Melting-point [° C.] |
|---|---|---|---|---|---|---|---|---|---|---|
| A | Cp$_2$ZrMe$_2$ | B(C$_6$F$_5$)$_3$ | 15 (59.5) | 30 (58.6) | 20 | 1 | 60 | 9.9 | 169 | 128.0 |
| 2 | Cp$_2$ZrMe$_2$ | HBNF | 9 (35.7) | 21 (36.3) | 20 | 1 | 30 | 6.4 | 359 | 127.2 |
| B | Cp$_2$ZrMe$_2$ | Bu$_3$NHBPH$_4$ | 9 (35.7) | 18 (35.6) | 20 | 1 | 60 | 0 | 0 | — |
| C | Cp$_2$Zr(C$_4$H$_6$) | B(C$_6$F$_5$)$_3$ | 10 (33.6) | 18 (35.2) | 20 | 1 | 30 | 9.2 | 541 | 128.3 |
| 3 | Cp$_2$Zr(C$_4$H$_6$) | HBNF | 10 (33.6) | 20 (34.5) | 20 | 1 | 30 | 10.1 | 591 | 129.7 |
| D | Me$_2$C(Cp)(1-indenyl)ZrMe$_2$ | B(C$_6$F$_5$)$_3$ | 10 (29.3) | 15 (29.3) | 20 | 1 | 60 | 0.6 | 20 | 127.5 |
| 4 | Me$_2$C(Cp)(1-indenyl)ZrMe$_2$ | HBNF | 10 (29.3) | 17 (29.4) | 20 | 1 | 60 | 1.2 | 40 | — |
| E | H$_2$C=C=CH=C(1-NMe$_2$)(1-Cp)(3-Cp)ZrMe$_2$ | B(C$_6$F$_5$)$_3$ | 10 (29.0) | 15 (29.3) | 20 | 1 | 60 | 0 | 0 | — |
| 5 | H$_2$C=C=CH=C(1-NMe$_2$)(1-Cp)(3-Cp)ZrMe$_2$ | HBNF | 10 (29.0) | 17 (29.4) | 20 | 1 | 60 | 0.4 | 14 | — |
| F | Me$_2$C(Cp)(1-indenyl)Zr(C$_4$H$_6$) | B(C$_6$F$_5$)$_3$ | 13 (35.6) | 22 (43.0) | 40 | 2 | 40 | 16.2 | 341 | — |
| 6 | Me$_2$C(Cp)(1-indenyl)Zr(C$_4$H$_6$) | HBNF | 10 (27.4) | 16 (27.6) | 40 | 2 | 40 | 22.2 | 608 | 106.3 |
| 7 | Me$_2$C(Cp)(1-indenyl)Zr(C$_4$H$_6$) | HBNF | 10 (27.4) | 16 (27.6) | 40 | 2 | 60 | 36.9 | 673 | 106.1 |
| G | Me$_2$C(Cp)(1-indenyl)ZrCl$_2$ | MAO | 13 (34.0) | 2100 (36200) | 40 | 2 | 40 | 18.2 | 411 | — |
| 8 | Me$_2$C(Cp)(1-indenyl)ZrMe$_2$ | HBNF | 10 (29.3) | 17 (29.4) | 40 | 2 | 40 | 13.8 | 354 | 129.2 |
| H | H$_2$C=C=CH=C(1-NMe$_2$)(1-Cp)(3-CP)ZrCl$_2$ | MAO | 17 (44.1) | — | 20 | 2 | 60 | 28.8 | 318 | 127.1 |
| 9 | H$_2$C=C=CH=C(1-NMe$_2$)(1-Cp)(3-CP)ZrMe$_2$ | HBNF | 10 (29.0) | 17 (29.4) | 40 | 2 | 15 | 5.6 | 386 | 129.3 |
| I | H$_2$C=C=CH=C(1-NMe$_2$)(1-Cp)(3-CP)ZrMe$_2$ | MAO | 19 (49.3) | — | 60 | 2 | 40 | 55.3 | 842 | 125.4 |

Polymerization of Propene

The polymerisation was carried out in the same manner as the polymerisation of ethene except that propylene was used as the monomer. The amounts of the novel activator used in the examples according to the present invention (activator: HBNF) and the comparative examples (activator: B(C$_6$F$_5$)$_3$) and the information on the polymers obtained are shown in table 2.

TABLE 2

| Example/ Comp. Example | Organometallic compound | Activator | Organometallic compound [mg(μmol)] | Activator) [mg(μmol)] | T [° C.] | P [bar] | Reaction-time [min] | Amount of polymer [g] | Activity [g/mmol Zr-bar-h] | Melting-point [° C.] | mmmm *) [%] |
|---|---|---|---|---|---|---|---|---|---|---|---|
| J | Me$_2$C(Cp)(1-indenyl)-Zr(C$_4$H$_6$) | B(C$_6$F$_5$)$_3$ | 13 (35.6) | 22 (43.0) | 40 | 2 | 60 | 31.8 | 446 | — | 10 |
| 10 | Me$_2$C(Cp)(1-indenyl)-Zr(C$_4$H$_5$) | HBNF | 11 (30.1) | 22 (38.0) | 40 | 2 | 90 | 10.2 | 113 | — | 12 |
| K | Me$_2$C(Cp)(1-indenyl)ZrCl$_2$ | MAO | 13 (34.0) | 2100 (36200) | 40 | 2 | 60 | 15.1 | 222 | — | 10 |
| L | Me$_2$Si(1-indenyl)$_2$Zr(C$_4$H$_6$) | B(C$_6$F$_5$)$_3$ | 15 (39.3) | 22 (43.0) | 40 | 2 | 45 | 63.6 | 1222 | — | 77 |
| 11 | Me$_2$Si(1-indenyl)$_2$Zr(C$_4$H$_6$) | HBNF | 11 (28.8) | 19 (32.8) | 40 | 2 | 45 | 81.9 | 1894 | 129.0 | 88 |
| M | Me$_2$Si(1-indenyl)$_2$ZrCl$_2$$^5$ | MAO | 9 (22.6) | 2100 (36200) | 40 | 2 | 45 | 201.8 | 6706 | — | 69 |
| 12 | H$_2$C=C=CH=C(1-NMe$_2$)(1-Cp)(3-Cp)ZrMe$_2$ | HBNF | 10 (29.0) | 18 (31.1) | 40 | 2 | 60 | 0 | 0 | — | — |
| N | H$_2$C=C=CH=C(1-NMe$_2$)(1-Cp)(3-CP)ZrCl$_2$ | MAO | 23 (59.7) | — | 20 | 2 | 180 | 30 | 85 | — | — |
| O | H$_2$C=C=CH=C(1-NMe$_2$)(1-Cp)(3-CP)ZrCl$_2$ | MAO | 25 (64.9) | — | 60 | 2 | 120 | 6.8 | 26 | — | — |

*) $^{13}$C-NMR-Analyse

We claim:

1. A process for preparing compounds of the formula (I):

$$(C_6R^1{}_5)_3MR^2 \quad (1)$$

where
- $R^1$ are identical or different and are each a hydrogen atom, a halogen atom, $C_1$–$C_{20}$-alkyl, $C_6$–$C_{14}$-aryl, $C_6$–$C_{14}$-aryl, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{10}$-haloalkyl, $C_6$–$C_{10}$-haloaryl, $C_2C_{10}$-alkynyl or $C_3$–$C_{20}$-alkylsilyl;
- M is an element of main group III of the Periodic Table of the Elements; and
- $R^2$ is a substituted or unsubstituted heterocycle; wherein the compounds of formula (I) are salt-like; the process comprising firstly reacting heterocycles $R^2$ containing elements of main group I or II of the Periodic Table of the Elements with compounds of the formula $(C_6C^1{}_5)_3M$ in a solvent to form compounds of the formula $[(C_6R^1{}_5)_3MR^2]$ which are subsequently protonated by reaction with a proton donor.

2. The process according to claim 1 wherein the heterocycle is pyrrolium, indolium or imidazolium.

3. The process according to claim 1 wherein M is aluminum or boron.

4. The process according to claim 1 wherein the heterocycle $R^2$ is unsubstituted or substituted by at least one halogen atom, $C_1$–$C_{20}$-alkyl, $C_1$–$C_{10}$-alkoxy, $C_2$–$C_{10}$-alkenyl, $C_7$–$C_{20}$-arylalkyl, $C_7C_{20}$-alkylaryl, $C_6$–$C_{10}$-aryloxy, $C_1$–$C_{20}$-haloalkyl, $C_6$–$C_{14}$-haloaryl, $C_2$–$C_{10}$-alkynyl or $C_3$–$C_{20}$-alkylsilyl.

5. The process according to claim 1 wherein the heterocycle $R^2$ is unsubstituted.

6. A process for preparing a catalyst system comprising contacting at least one organometallic compound (A) of a transition metal; at least one compound of the formula (I) prepared by a process according to claim 1; optionally an alkyl compound (B) of an element of group III or IV of the Periodic Table of the Elements; and, optionally at least one support component (C).

7. The process according to claim 6 wherein in a first step A, the at least one support component (C) is first reacted with a first alkyl compound (B) of the formula (III),

(III)

wherein
wherein $R^{20}$ are identical or different and can be a halogen atom, a hydrogen atom or a $C_1$–$C_{40}$ group,
thereby forming a pretreated support wherein the pretreated support is optionally washed and/or dried;

mixing in a further step B the pretreated support with the at least one organometallic compound (A) of a transition metal complex of formula (II),

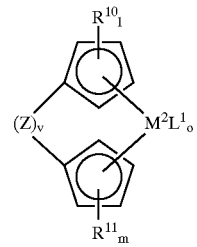

(II)

where
- $M^2$ is a metal of transition group III, IV, V or VI of the Periodic Table of the Elements,
- $R^{10}$ are identical or different and are each a hydrogen atom or $Si(R^{12})_3$, where $R^{12}$ are identical or different and are each a hydrogen atom or a $C_1$–$C_{40}$ group, or $R^{10}$ is a $C_1$–$C_{30}$ group, or two or more radicals $R^{10}$ may be joined to one another in such a way that the radicals $R^{10}$ and the atoms of the cyclopentadienyl ring which connect them form a $C_4$–$C_{24}$ ring system which may optionally be substituted,
- $R^{11}$ are identical or different and are each a hydrogen atom or $Si(R^{12})_3$, where $R^{12}$ are identical or different and are each a hydrogen atom or a $C_1$–$C_{40}$ group, or $R^{11}$ is a $C_1$–$C_{30}$ group, or two or more radicals $R^{11}$ may be joined to one another in such a way that the radicals $R^{11}$ and the atoms of the cyclopentadienyl ring which connect them form a $C_4$–$C_{24}$-ring system which may optionally be substituted,
- | is 5 when v=0, and | is 4 when v=1,
- m is 5 when v=0, and m is 4 when v=1,
- $L^1$ may be identical or different and are each a hydrogen atom, a $C_1$–$C_{10}$-hydrocarbon group, a halogen atom or $OR^{16}$, $SR^{16}$, $OSi(R^{16})_3$, $Si(R^{16})_3$, $P(R^{16})_2$ or $N(R^{16})_2$, where $R^{16}$ is a halogen atom, a $C_1$–$C_{10}$-alkyl group, a halogenated $C_1$–$C_{10}$-alkyl group, a $C_6$–$C_{20}$-aryl group or a halogenated $C_6$–$C_{20}$-aryl group, or $L^1$ is a toluensulfonyl, trifluoroacetyl, trifluoroacetoxyl, trifluoromethanesulfonyl, nonafluorobutanesulfonyl or 2,2,2-trifluoroethanesulfonyl group,
- o is an integer from 1 to 4
- Z is a bridging structural element between the two cyclopentadienyl rings and
- v is 0 or 1 and the at least one compound of the formula (I); and reacting in a further step C the material obtained in step B with a second alkyl compound (B) of the formula (III).

* * * * *